United States Patent
Sullivan

(10) Patent No.: US 9,733,703 B2
(45) Date of Patent: Aug. 15, 2017

(54) SYSTEM AND METHOD FOR ON-AXIS EYE GAZE TRACKING

(71) Applicant: Mirametrix Inc., Westmount (CA)

(72) Inventor: Nicholas J. Sullivan, Montreal (CA)

(73) Assignee: Mirametrix Inc., Montreal (CA)

( * ) Notice: Subject to any disclaimer, the term of this patent is extended or adjusted under 35 U.S.C. 154(b) by 130 days.

(21) Appl. No.: 14/626,288

(22) Filed: Feb. 19, 2015

(65) Prior Publication Data

US 2015/0160726 A1  Jun. 11, 2015

Related U.S. Application Data

(63) Continuation of application No. PCT/CA2014/050282, filed on Mar. 17, 2014.

(60) Provisional application No. 61/802,881, filed on Mar. 18, 2013.

(51) Int. Cl.
| | |
|---|---|
| G06K 9/00 | (2006.01) |
| G06F 3/01 | (2006.01) |
| G02B 27/00 | (2006.01) |
| G09G 5/00 | (2006.01) |
| A61B 3/113 | (2006.01) |
| H04N 13/04 | (2006.01) |

(52) U.S. Cl.
CPC ......... *G06F 3/013* (2013.01); *G02B 27/0093* (2013.01); *G06K 9/00604* (2013.01); *A61B 3/113* (2013.01); *H04N 13/0484* (2013.01)

(58) Field of Classification Search
CPC ............... G06F 3/00; G06K 9/00; A61B 3/00
USPC ......... 382/103, 115–117, 236; 348/169, 170, 348/171, 172, 352; 345/156; 351/209
See application file for complete search history.

(56) References Cited

U.S. PATENT DOCUMENTS

| | | |
|---|---|---|
| 3,804,496 A | 4/1974 | Crane et al. |
| 4,950,069 A | 8/1990 | Hutchinson |
| 5,231,674 A * | 7/1993 | Cleveland ............ A61B 3/113 351/210 |
| 6,134,339 A | 10/2000 | Luo |

(Continued)

FOREIGN PATENT DOCUMENTS

| | | |
|---|---|---|
| CA | 2545202 C | 1/2014 |
| CN | 101951828 A | 1/2011 |
| WO | 2007092512 A2 | 8/2007 |

OTHER PUBLICATIONS

Yoo, H. D. et al.; "A novel non-intrusive eye gaze estimation using cross-ration under large head motion"; Computer Vision and Image Understanding 98 (2005) 25-51; Elsevier; Accessed online Jun. 24, 2014 from http://www.shoutwiki.com/w/images/wearable/9/9f/Yoo_2005_Computer-Vision-and-Image-Understanding.pdf.

(Continued)

*Primary Examiner* — Abolfazl Tabatabai
(74) *Attorney, Agent, or Firm* — Brett J. Slaney; Blake, Cassels & Graydon LLP

(57) ABSTRACT

A system and method are provided for performing eye gaze tracking. The system is configured for and the method comprises optimizing illumination of a scene for a single on-axis imaging apparatus, capturing an image using the single on-axis imaging apparatus under the optimized illumination, and processing the captured image to perform a gaze estimation. Dynamic illumination control, eye candidate detection and filtering, and gaze estimation techniques are also provided.

36 Claims, 20 Drawing Sheets

(56) References Cited

U.S. PATENT DOCUMENTS

| | | | |
|---|---|---|---|
| 6,634,749 B1* | 10/2003 | Morrison | A61B 3/113 351/209 |
| 7,362,885 B2 | 4/2008 | Hammoud | |
| 7,762,665 B2 | 7/2010 | Vertegaal et al. | |
| 8,077,914 B1* | 12/2011 | Kaplan | A61B 3/113 351/209 |
| 8,096,660 B2 | 1/2012 | Vertegaal et al. | |
| 8,292,433 B2 | 10/2012 | Vertegaal et al. | |
| 8,322,856 B2 | 12/2012 | Vertegaal et al. | |
| 8,339,446 B2 | 12/2012 | Blixt et al. | |
| 8,342,687 B2 | 1/2013 | Blixt et al. | |
| 8,343,067 B2 | 1/2013 | Jones et al. | |
| 8,348,429 B2* | 1/2013 | Walsh | A61B 3/1005 351/204 |
| 2010/0007601 A1 | 1/2010 | Lashina et al. | |
| 2010/0057059 A1 | 3/2010 | Makino | |
| 2011/0175932 A1 | 7/2011 | Yu et al. | |

OTHER PUBLICATIONS

Norman, P.; International Search Report from corresponding PCT Application No. PCT/CA2014/050282; search completed Jun. 27, 2014.

English translation of search report from corresponding Chinese Application No. 201480028893.9, issued Jan. 18, 2017.

\* cited by examiner

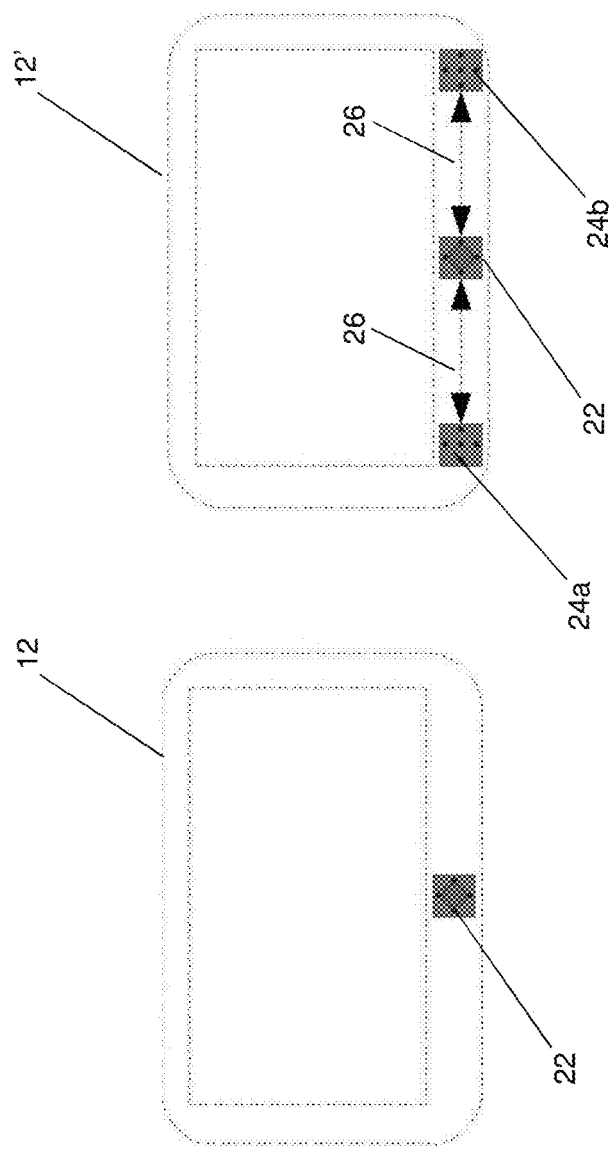

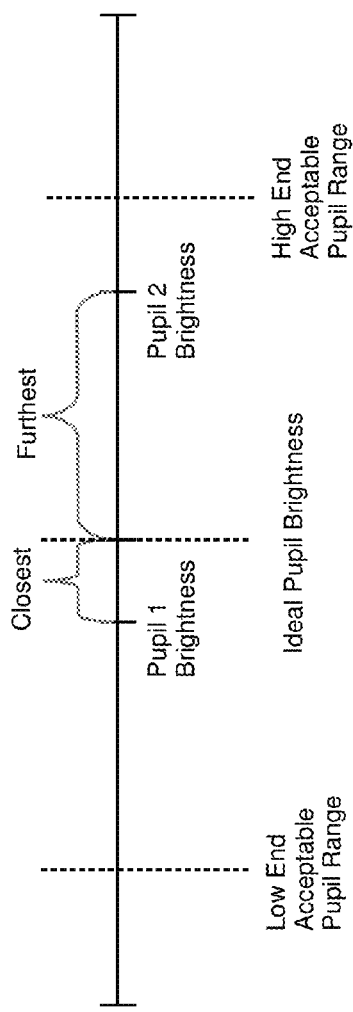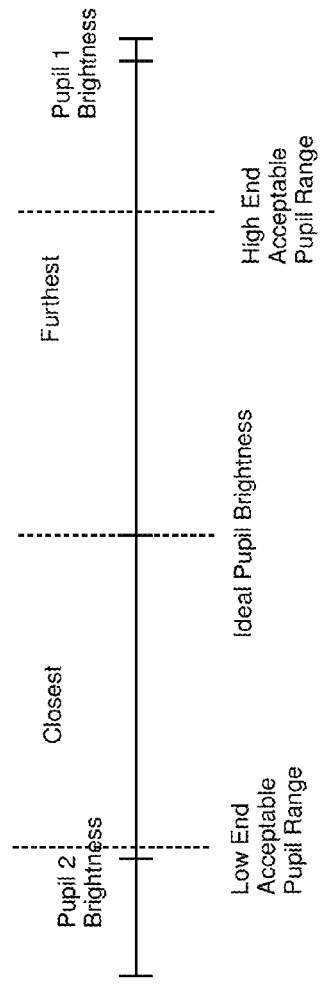
FIG. 9
FIG. 10 ns have 60 FIG. 17 illustrates an application of thresholding to the
SYSTEM AND METHOD FOR ON-AXIS EYE GAZE TRACKING

CROSS-REFERENCE TO RELATED APPLICATIONS

This application is a continuation of International PCT Application No. PCT/CA2014/050282 filed on Mar. 17, 2014 which claims priority from U.S. Provisional Application No. 61/802,881 filed on Mar. 18, 2013, both incorporated herein by reference.

TECHNICAL FIELD

The following relates to systems and methods for on-axis eye gaze tracking.

DESCRIPTION OF THE RELATED ART

Common techniques for interaction between humans and machines include hand-operated user interface devices, such as keyboards, buttons, joysticks and pointing devices (e.g., mouse, stylus, etc.). Recent developments in eye-gaze tracking systems can determine a line-of-sight (LOS) vector of an individual's eye. This LOS information can be used as a control tool for human machine interaction.

There are known to be two general types of gaze estimation procedures for a user to a location in space (e.g., screen), namely functional mappings and 3D models. In functional mappings, screen-point and feature vector pairs are obtained (usually via a calibration procedure), with each pair containing the feature vector obtained from a user when the user was gazing at the provided point on the screen. These two data sets are then used to approximate a gaze mapping function from the feature vector to the screen position.

In 3D model-based approaches, the extracted eye features are used in conjunction with a chosen model of the eye to estimate the optical axis of the eye. This axis determines the angular position of the eye in space, and can be used in conjunction with the known divergence of a user's visual axis to estimate where the user is looking in space.

There can be a number of advantages to using eye-gaze tracking information as a control tool. For example, such advantages can include: an intuitive link between the visual system of the eye and the resultant images in the brain; the speed of eye movement relative to moving a hand-operated interaction device (i.e. users typically look at the desired destination of a hand-operated device prior to moving the hand-operated device); and the possibility that eye-gaze tracking techniques may be used by severely disabled individuals, to name a few.

A number of other applications for eye-gaze tracking systems can include, for example: psychological and physiological research into the connection between eye movements and perceptual and/or cognitive processes; an analysis of driver awareness; research into the effectiveness of advertising and website layouts; and gaze contingent displays, to name a few.

Typically, many existing gaze tracking technologies have been known to employ systems that operate as follows, wherein provided image data is analyzed for finding eyes, the found eyes have particular features extracted, and the features are used to estimate a point of gaze on the screen. However, these systems typically employ multiple illumination sources and one or more imaging systems in order to determine the user's POG. These systems tend to contain both on-axis and off-axis illumination sources, using an image differencing method to detect and track eyes in the scene. From this, the pupil center and multiple corneal reflections from the illumination sources (also known as Purkinje images) are extracted as eye features and used to determine the POG of the user on the screen.

SUMMARY

In one aspect, there is provided a method of performing eye gaze tracking, the method comprising: optimizing illumination of a scene for a single on-axis imaging apparatus; capturing an image using the single on-axis imaging apparatus under the optimized illumination; and processing the captured image to perform a gaze estimation.

In other aspects, there are provided computer readable media and systems configured to perform the method.

BRIEF DESCRIPTION OF THE DRAWINGS

Embodiments will now be described by way of example only with reference to the appended drawings wherein:

FIG. 2 is an example of an on-axis equipped electronic device;

FIG. 3 is an example of an on-and-off axis equipped electronic device;

FIG. 9 is a schematic diagram illustrating a procedure for idealizing pupils;

FIG. 10 is a schematic diagram illustrating another procedure for idealizing pupils;

DETAILED DESCRIPTION

Figure 1:
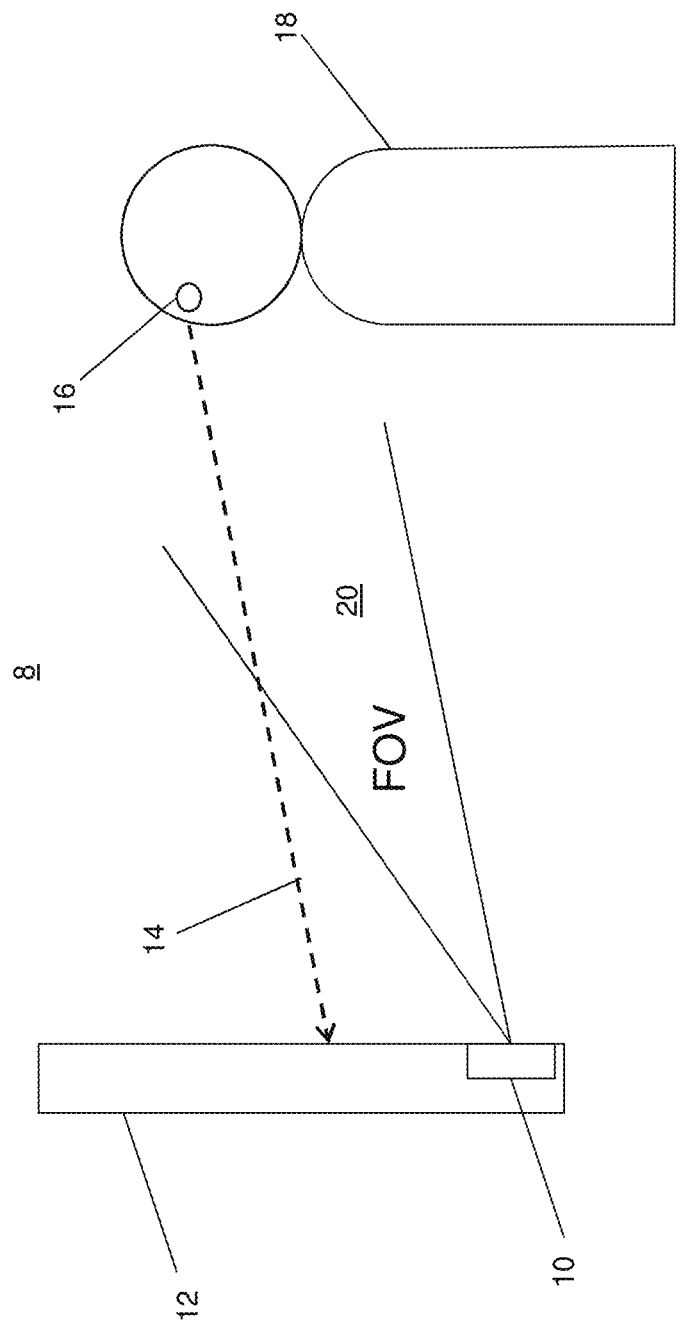
FIG. 1 is a schematic diagram of an environment in which a gaze tracking system is incorporated into an electronic device for tracking the gaze of a user.

It will be appreciated that for simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

It has been found that most extant infrared based eye-tracking systems require both on-axis and off-axis illumination sources in order to reliably track a user's pupils. The methods and algorithms explained hereafter describe a system for an eye gaze tracker having a single on-axis sensor with on-axis illumination source(s). It has been recognized that the ability to provide an eye tracking system having only a single sensor allows for the creation of an eye-tracking system module which can be sized to be accommodated within a wide variety of electronic devices, particularly handheld or personal electronic devices. For example, the system described herein can be configured to be accommodated with a form factor similar to a standard laptop webcam or portable device camera, which can be conveniently interfaced in a laptop or multimedia device as an intuitive additional human machine interface. It can be appreciated that while the example described herein are illustrated in an on-axis-only configuration, the principles described can equally be applied to on-and-off-axis eye gaze trackers to improve their reliability and decrease false positive detection rates.

There is provided a system that is configured for sensing and tracking eye-gaze characteristics and to use information obtained therefrom to estimate a point-of-gaze. Such a system is particularly advantageous in configurations using a single on-axis sensor to capture eye-gaze data.

The following provides a system and computer executable instructions and operations to be implemented by such a system for performing dynamic illumination of a subject's eyes, on-axis candidate detection techniques, on-axis candidate filtering processes, and on-axis gaze determination techniques as discussed in greater detail below. As will be described in greater detail below, the on-axis eye candidate filtering and on-axis eye candidate detection techniques may be generally referred to herein as eye detection and tracking.

The on-axis gaze determination techniques may also be referred to herein as methods by which extracted features from an image are used to estimate a gaze on a screen. The dynamic illumination may be considered a parallel process or technique that modifies parameters of the apparatus being used to perform eye tracking to achieve acceptable image quality for gaze tracking. It can be appreciated that the techniques described herein may be incorporated into any suitable eye gaze tracking system. Particularly, the dynamic illumination and eye candidate filtering algorithms can be independently modularized and used in any eye gaze tracking system to improve reliability and potentially increase the range of users under which gaze tracking will be feasible and/or functional.

The system and methods described herein provide various advantages. For example, the system and methods described herein can be employed to reduced sizing, increase modularization, and increase the percentage of users under which gaze tracking is feasible.

It has been found that by allowing a reliable eye tracking device to function on a single camera with a single, coaxial illumination source, one constricts the sizing constraints of the hardware device to that of the camera itself. This is because the inclusion of a coaxial illumination source is often minimal in comparison to the sizing requirements of off-axis illumination, which is physically constrained by the distance required for the illumination sources to not be co-axial in functionality.

Moreover, it has been found that a significant increase in modularability (i.e. an ability to modularize) can be achieved since a depth calculation method is independent of the particular setup used. For example, once a camera module is chosen in a design, the system described herein can be interfaced with the camera module in a manner similar to interfacing with a standard webcam. This is particularly advantageous when compared to off-axis configurations that require more complex set up and interfacing to be used between the illumination sources and camera module, e.g., for synchronization, etc. For example, the distance of the off-axis illumination sources often limits the range in which an eye gaze tracker can function, since the distance metric is achieved via triangulation. It may be noted that this problem has also been found for eye tracking systems using two cameras, since two camera systems use the distance between the cameras to triangulate the distance the user is from the system.

The following techniques can advantageously enable an increased amount of variability in eye parameters and therefore be applicable to a larger user base. The dynamic illumination technique described herein enables the eye gaze system to scan a more complete range of permissible illumination settings in order to find a user, whereas previous systems have been found to have a fixed range thus limiting the potential base of users. It has also been found that the system described herein can be adapted to handle other use cases such as where a user is wearing eyeglasses, by applying the eye candidate filtering algorithm to accurately reject pupil-like objects.

Turning now to the figures, FIG. 1 illustrates a gaze tracking environment 8 (i.e. any environment in which gaze tracking is performed) in which an on-axis gaze tracking system 10 is incorporated into an electronic device 12. In the example shown in FIG. 1, the gaze tracking system 10 tracks the gaze 14 of one or more eyes 16 of a user 18 which is directed towards at least a component of the electronic device 12 (e.g., display screen). The gaze tracking system 10 includes one or more imaging components (described for example below) having a field of view (FOV) 20 that allows for imaging the eye(s) 16 of the user 18.

FIG. 2 illustrates an external front view of the on-axis equipped electronic device 12 shown in FIG. 2. When compared to the on-and-off axis equipped electronic device 12' shown in FIG. 3, a reduced complexity is apparent. As shown in FIG. 2, the on-axis gaze tracking system 10 includes an imaging apparatus 22 that provides illumination and at least one lens element (not shown) for capturing images within the FOV 20. The on-and-off-axis equipped electronic device 12' shown in FIG. 3 may include the on-axis gaze tracking system 10 herein described (with imaging apparatus 22 shown in FIG. 3), and includes additional off-axis imaging apparatus 24 (two apparatus 24a, 24b flanking on-axis apparatus 22 in FIG. 3), and synchronization components 26 between imaging apparatus 22, 24. It can be appreciated that the on-axis gaze tracking system 10 is capable of being incorporated into smaller devices without requiring the additional separation for off-axis components. Moreover, the need for synchronization between components is greatly minimized if not eliminated.

Figure 4:
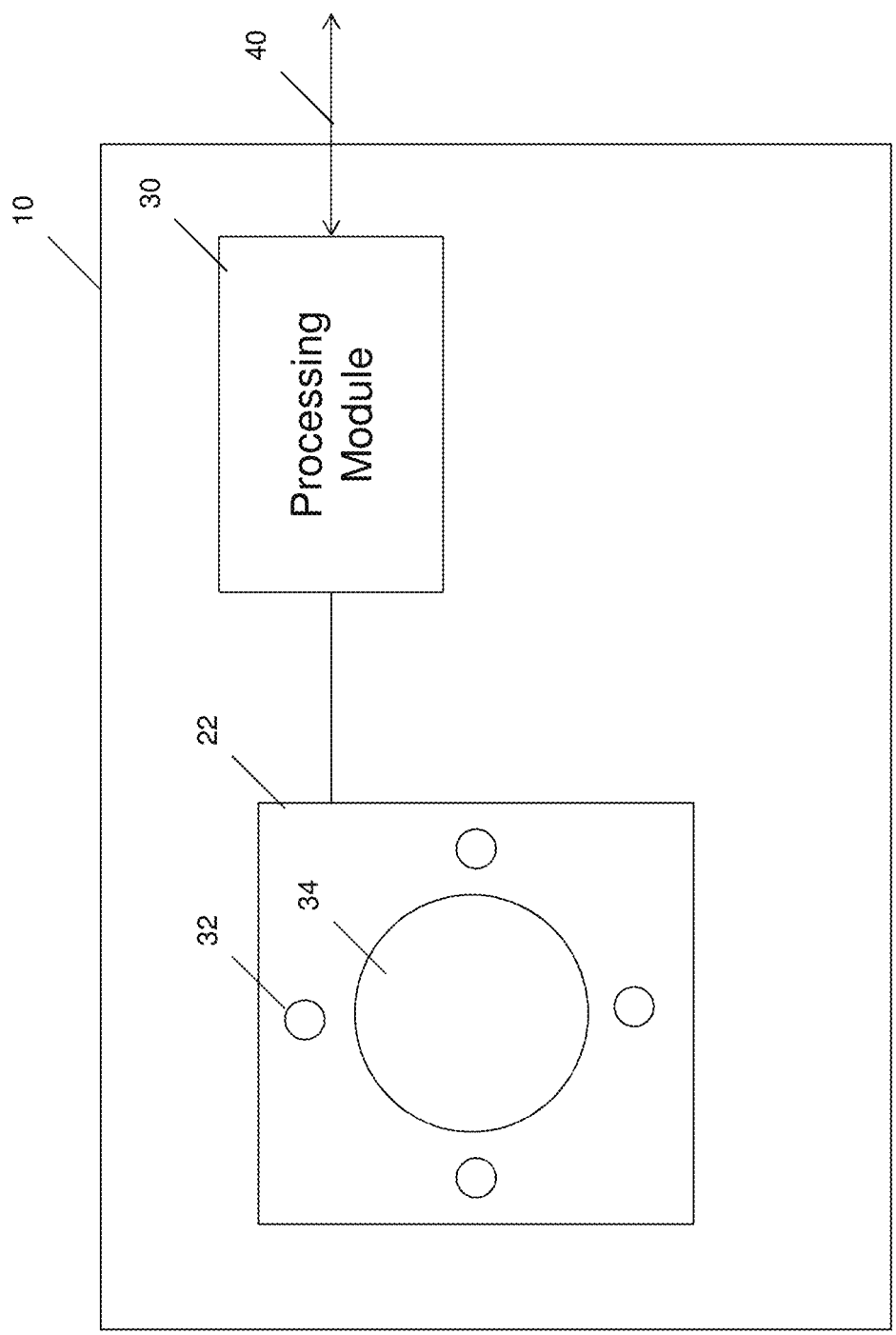
FIG. 4 is an example of a configuration for a gaze tracking system.

An example of a configuration for the on-axis gaze tracking system 10 is shown in FIG. 4, which includes the on-axis imaging apparatus 22 and a processing module 30. The processing module 30 may generally represent any one or more components, modules, sets of programming instructions, etc. for performing the various techniques, processes, methods and algorithms (terms used interchangeably) described herein. The processing module 30 is coupled to the imaging apparatus 22 to received captured images and to provide instructions and/or data for controlling use of the imaging apparatus 22 as described in greater detail below. The on-axis imaging apparatus 22 includes an imaging module 34 (e.g., a camera), and one or more illumination sources 32 (e.g., a series of infrared LEDs surrounding a camera). The on-axis gaze tracking system 10 also includes a communication bus or other connection 40 for interfacing with the electronic device 12, e.g., to provide eye gaze as an input to an application or process on the electronic device 12.

Figure 5:
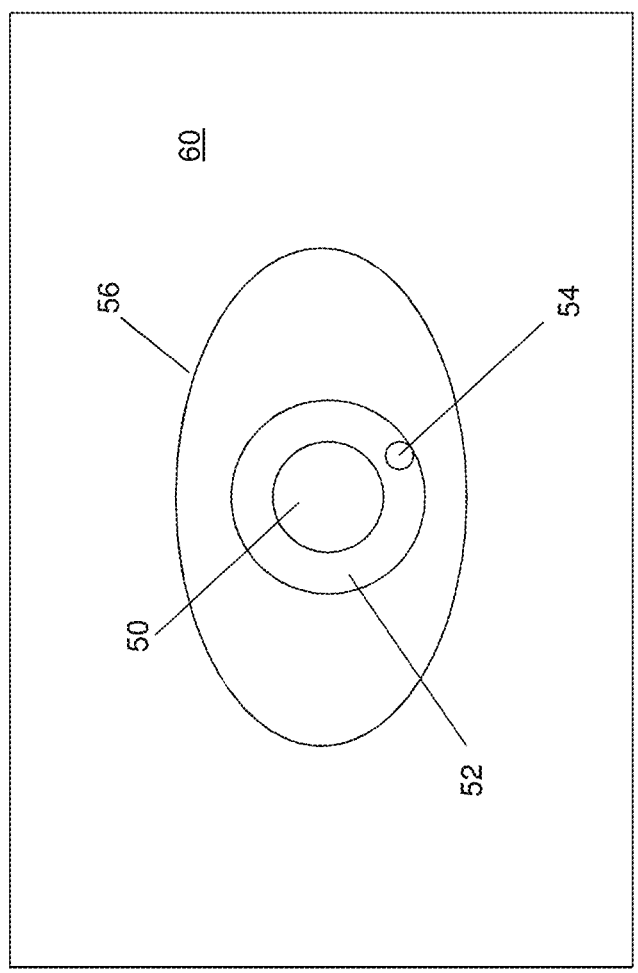
FIG. 5 is a schematic illustration of an eye in an image.

The imaging apparatus 22, 24 captures images that allow for the detection of the eyes of a user. FIG. 5 is an example of an eye that may be imaged under either co-axial or on-axis illumination. In FIG. 5, the eye includes a pupil 50, an iris 52, a glint 54, sclera 56, and surrounding skin 60.

Figure 6:
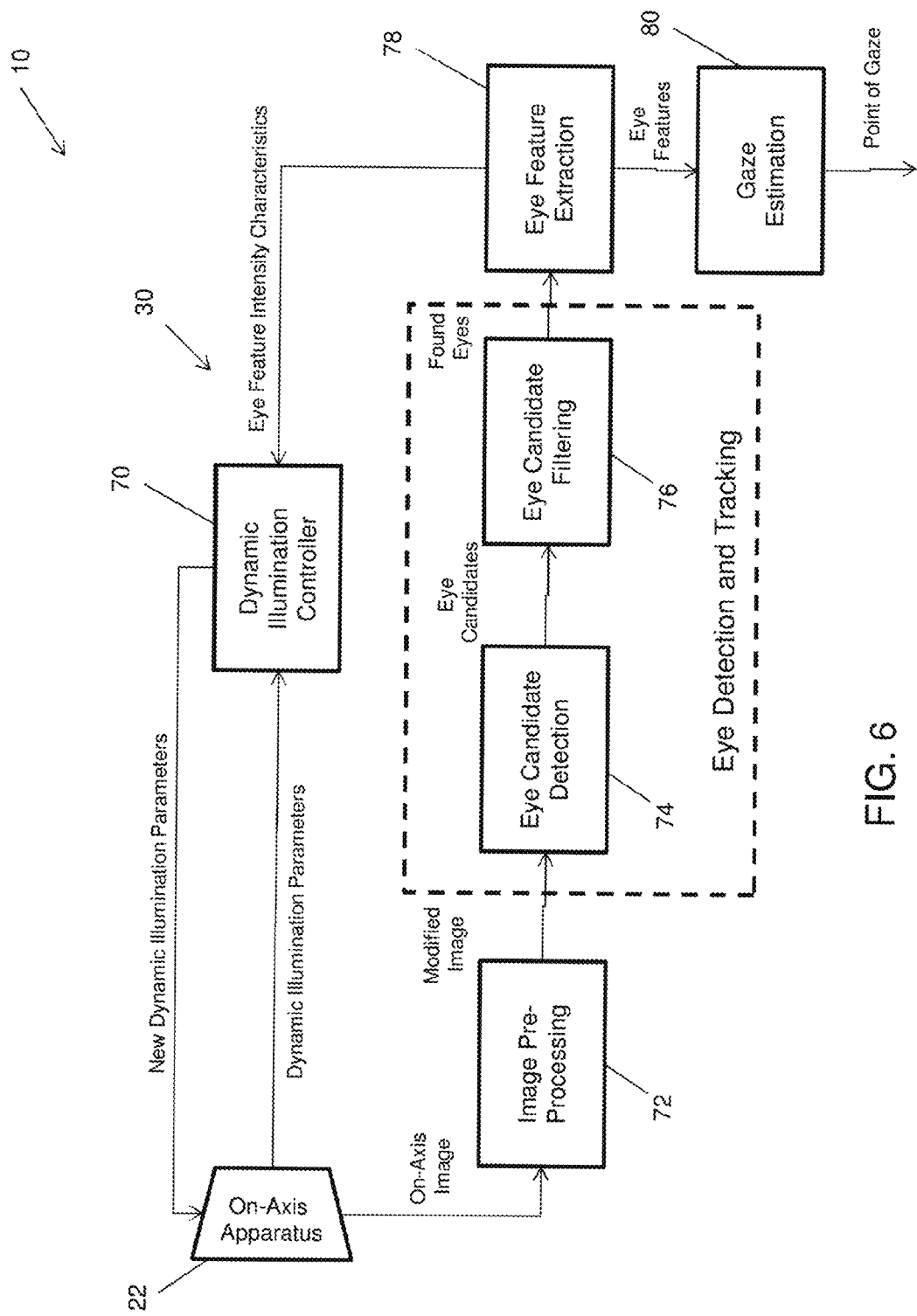
FIG. 6 is block diagram illustrating an example of a configuration for a gaze tracking system.

Turning now to FIG. 6, an example of a configuration for the gaze tracking system 10 is shown. In the configuration shown in FIG. 6, various functional blocks of the processing module 30 are shown coupled to the imaging apparatus 22. The imaging apparatus 22 captures an on-axis image, which is provided to an image pre-processing block 72 for performing image enhancement techniques to the on-axis image. These can include any method of modifying the original image, to permit easier eye detection and tracking, or eye feature extraction. Examples of this could include de-noising, de-blurring, contrast enhancement, and edge enhancement of the image. The pre-processing produces a modified image that is provided to an eye detection and tracking stage, in which eye candidate detection 74 is performed on the modified image to determine eye candidates, and eye candidate filtering 76 is performed on the eye candidates to determine "found" eyes. The found eyes are provided to an eye feature extraction block 78 to determine eye features, which are provided to a gaze estimation block 80 to generate a point of gaze output, e.g., to be provided to an application or process in the electronic device 12. As shown in FIG. 6, in parallel, a dynamic illumination controller 70 can be used to obtain dynamic illumination parameters from the imaging apparatus 22 and eye feature intensity characteristics from the eye feature extraction block 78 to generate new dynamic illumination parameters to refine the illumination procedure on an on-going basis (e.g., to achieve an optimized or ideal illumination).

In the discussion and examples below, the term "blob" may be used in reference to a region of a digital image with common properties such that the region is considered a distinct object. The digital image may be analyzed and filtered by a predetermined metric to be converted into a binary image (i.e. an image with pixels with a range of two values). In these cases, a binary blob is extracted. It can also be appreciated that in the following discussion, when discussing an on-axis apparatus, any combination of an imaging system and single co-axial illumination source is applicable, and the example shown in FIG. 4 is for illustrative purposes only. For example, a single illumination source may include any combination of smaller illumination sources such as LEDs to create a single unified illumination source, or a single large source.

Dynamic Illumination

An example of a dynamic illumination process that may be performed by the dynamic illumination controller 70 will now be described referring to FIGS. 7A and 7B. The dynamic illumination process may function similar to an automatic gain control system, to ensure that the signal is within an acceptable illumination range, via a feedback-control loop in the system 10. In this example, the dynamic illumination process takes as an input one or more signal amplitude indicators at time step t, and one or more illumination variation parameters, and determines updated illumination parameters in order to improve the signal amplitude at time step (t+1). The signal amplitude indicators for the dynamic illumination process in this example are intensity characteristics of the user's eyes, and as such can be deemed eye feature intensity parameters. Since one or more users may not always be contained within the scene, a multi-state system can also be configured to allow for such situations as shown in FIG. 7B.

The objective of the dynamic illumination controller 70 is to modify the effective scene illumination such that the user's eyes are at an optimized or "ideal" illumination. By optimizing the scene illumination, the dynamic illumination controller 70 allows the gaze tracking system 10 to function accurately on a larger range of users, since there is a large amount of variation in users' pupil retro-reflectivity and having fixed camera parameters usually results in other gaze tracking systems not functioning accurately on a portion of the human population.

For the purpose of the following discussion, the following terms may be clarified:

Signal Amplitude Indicator:

this can signify any intensity indicator of the signal, such as the average intensity of a subsection of the image. For the purpose of the described dynamic illumination system, the intensity distribution of an extracted eye feature is used as the amplitude indicator. The system assumes a relationship between a desired ideal illumination and a given signal amplitude indicator's values. As an example, a dynamic illumination system could use the average intensity of a user's found pupils as its signal amplitude indicator, attempting to drive them as close as possible to half of the intensity range.

Illumination Variation Parameter:

this can signify any parameter available to the on-axis apparatus allowing modification of the quantity of light stored by a camera during a given time step t. Thus, an illumination variation parameter can involve a parameter controlling the amount of illumination output by the on-axis illumination source during a given time step t, or one controlling the amount of illumination that is stored by the camera sensor. An example of the former could be the amount of current passed to an LED illumination source; an example of the latter could be the shutter speed duration of an imaging system.

Eye Feature Brightness/Intensity:

When referring to a particular eye feature, we use the terms brightness and intensity interchangeably to signify the measured intensity of said feature by the imaging system. As an example, an on-axis image obtained from an on-axis apparatus may contain a user's pupils at an average intensity of 200 (as stored in an 8-bit unsigned greyscale image). Thus, the average pupil brightness or pupil intensity of said user's eyes in this image would be 200. Note that by average intensity, we mean the average of the pixel values delineated as belonging to the user's pupils.

On-Axis/Coaxial Illumination:

A coaxial illumination source refers to a source whose distance from the imaging system's optical axis is small enough that the reflected light returning to the system is substantially parallel to the axis of the optical system.

Ideal Illumination:

defined herein refers to an illumination state under which the user's eye features are easily differentiable from each other. Particularly, an ideal illumination can be considered an illumination setting where the desired eye features are illuminated enough such that they can be extracted by a computer vision system and are readily differentiable from other false positives in the scene. For the sake of clarity, although the following discussion relates to on-axis only gaze tracking systems 10, the principles of dynamic illumination may equally be applied to different configurations and different illumination criteria.

On-Axis Ideal Illumination:

refers to an illumination state under which the user's pupils are easily differentiable from its iris and the corneal glint. This allows the pupils to be easily segmented out from other objects in the scene, as well as facilitates extraction of other eye features used for gaze tracking (such as the corneal glint, and limbus boundary). The ideal illumination concept follows from the differences in the reflective properties of the sclera, skin, pupil, pupil glint, and iris of a user. For all users under on-axis illumination, the order of reflectivity from lowest to highest is typically: iris 52<sclera 56~skin 60~pupil 50<corneal glint 54 (where ~ denotes an approximation, and <denotes lesser than—see also FIG. 5). It may be noted that although each user's pupil reflectivity properties may be quite different, the difference between pupil reflectivity and iris reflectivity is typically large enough in most if not all cases, that the relationships in reflectivity described herein should hold true.

In general, a method for having a user's eyes at an on-axis ideal illumination can be described as follows: set the apparatus illumination properties such that the user's pupils are at a value corresponding to the midpoint of the range of the camera sensor. For example, for a camera sensor supplying an 8-bit digital image (0-255), the system's illumination settings can be modified such that the pupil is consistently at a value of 128. In this example, by doing so, the system 10 can aim to achieve the following:

a) The pupil not being over-exposed, and as such can easily be distinguished from the corneal glint and obstructing objects such as glasses glare (which end up as over-saturated blobs in the image);

b) The pupil not being under-exposed, and as such eye features of interest for gaze tracking (such as the corneal glint and limbus boundary) are illuminated enough to be distinguishable in the scene; and c) The iris, being the least reflective face property, being roughly within the lowest ¼th of the image range and therefore easily distinguishable.

In one example implementation of the dynamic illumination process herein described can take as input a scene's average pupil intensities as the signal amplitude parameter, and the current camera parameters, which in the described prototype uses shutter speed and gain. It may be noted that the process described herein may use camera parameters as the illumination variation parameters, as opposed to modifying the illumination source or other methods of modifying the scene's illumination. An objective of this process may therefore be to modify the effective scene illumination to approximate "ideal" conditions, and as such can be implemented via any combination of camera intensity parameters and illumination sources. For the sake of clarity and conciseness, the dynamic illumination process can be described with the illumination variation parameters used being camera gain and camera shutter duration. As described earlier, the dynamic illumination system can consist of any 1 to n illumination variation parameters. Thus, it should be simple to imagine such a defined system consisting solely of the camera shutter duration or gain.

It may also be noted that the dynamic illumination algorithm described herein may use the user's pupil intensity characteristics as the signal indicator parameters of the system 10. Given the known reflectance properties of different features of the eyes, any number of other features could be used as the indicator parameters of this system 10. However, due to the nature of the proposed system, the ease of extracting said parameters, and the described "ideal" illumination state, this feature is used in the described embodiment.

Figure 7A:
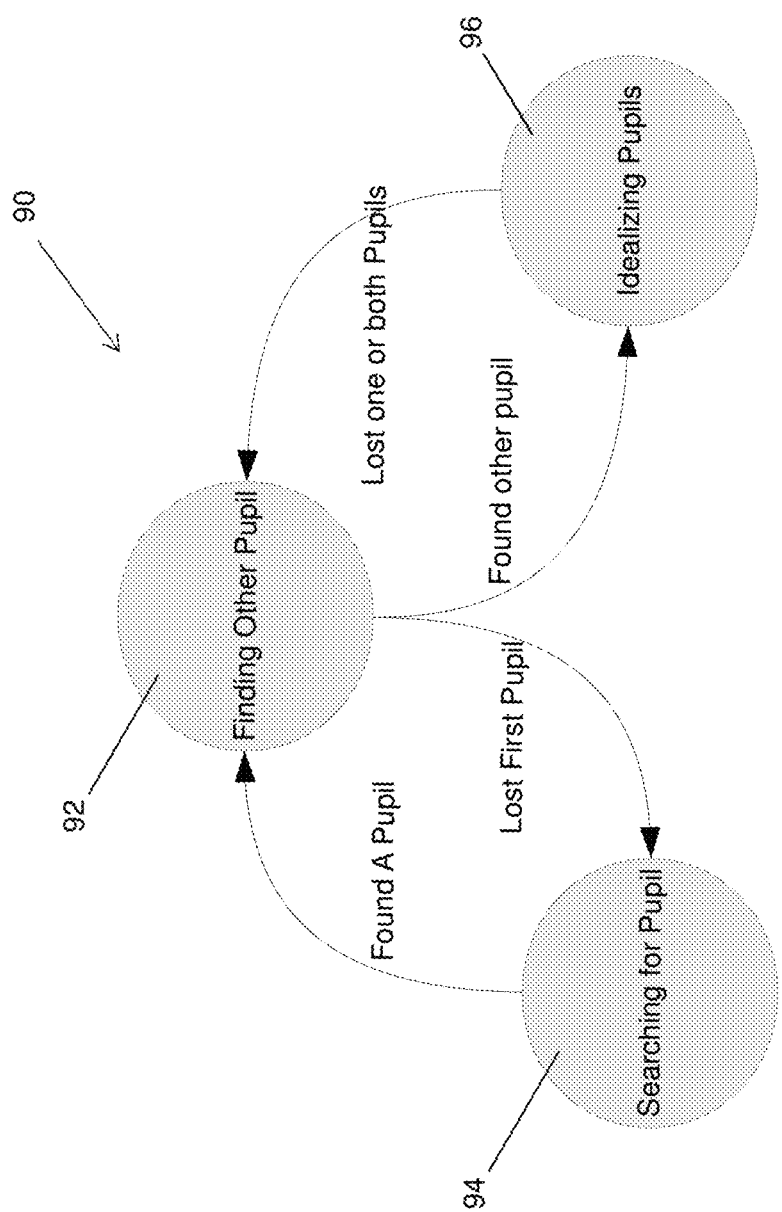
FIG. 7A is a state diagram illustrating application of a dynamic illumination procedure.
Figure 7B:
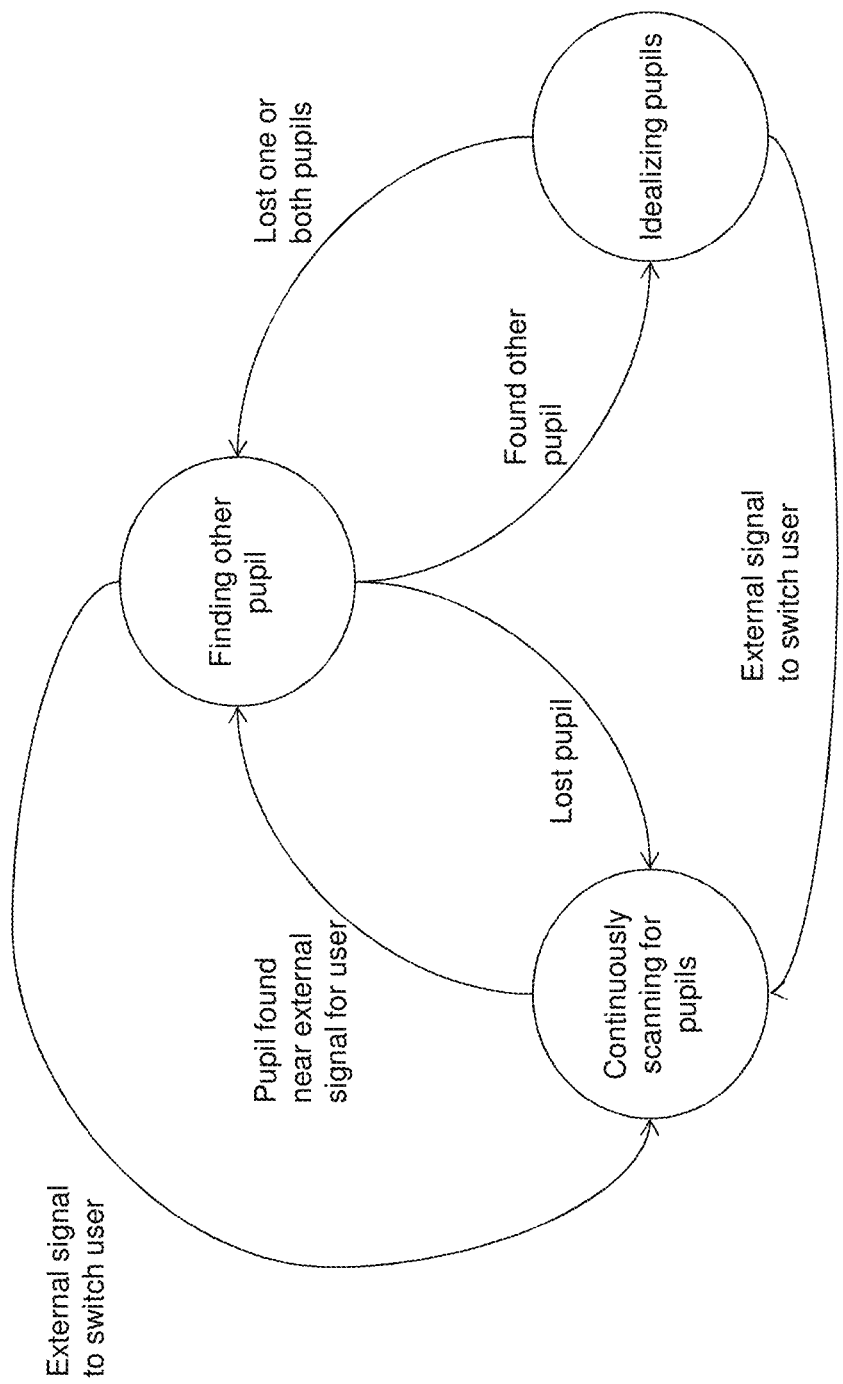
FIG. 7B is a state diagram illustrating application of a dynamic illumination with multiple users in the scene.

FIG. 7A illustrates the dynamic illumination process using a state diagram 90 having three states. Each state takes the pupils for analysis and determines whether or not to modify the camera intensity parameters. This example assumes that the system 10 expects only one user to be tracked in the scene at any given point in time. The state diagram 90 can therefore be modified to a configuration for tracking a particular user when multiple users are in the scene, as shown in FIG. 7B Searching For Pupil In the initial state of the dynamic illumination process, it can be assumed that no pupils have been found. In order to locate a pupil at 94, the dynamic illumination controller 70 cycles through different camera parameter settings until a pupil is found. In one example, the dynamic illumination controller 70 cycles through the full camera shutter duration range twice, switching the camera gain between 33% and 66% of its range at each cycle. A number of different shutter duration and gain combinations can be stored in a circular buffer and cycled through. A queue of found pupil intensities can also be created. At each iteration where a pupil is found, the pupil brightness is added into the queue. The dynamic illumination process cycles through the circular buffer, changing the camera shutter duration to the new setting each time, until the queue is the size of the circular buffer, or no pupils are found and the queue is non-empty; that is, the pupil(s) have been found under a previously tested shutter duration. At this point, the process examines the queue searching for the pupil brightness that is closest to the ideal pupil brightness, sets the shutter duration accordingly, and moves to the "Finding Other Pupil" state 92 shown in FIG. 7A.

By performing the above operations, the dynamic illumination process aims to choose the optimal shutter duration for the scene.

Finding Other Pupil

Figure 8:
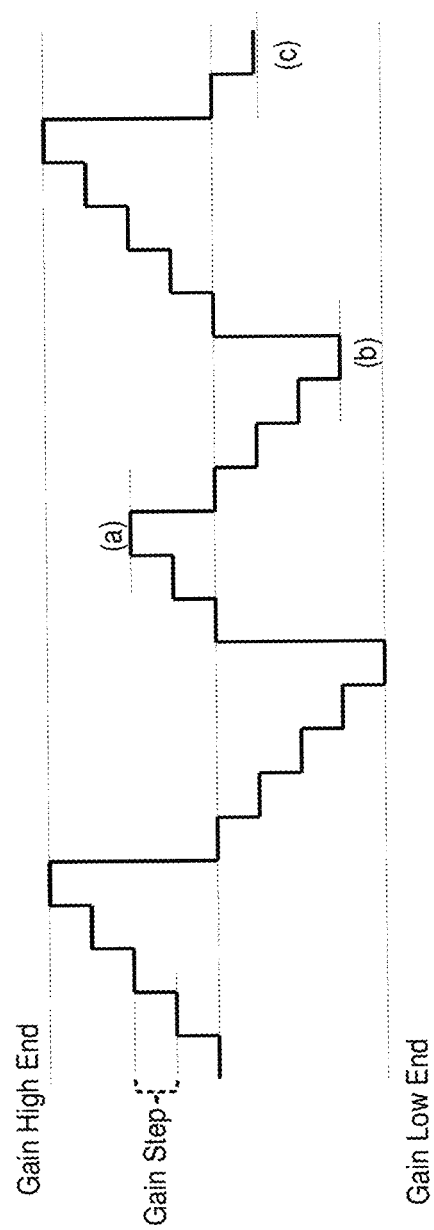
FIG. 8 is a schematic diagram illustrating a procedure for finding a second pupil.

In the finding other pupil state 92, the objective is to locate the user's other pupil while avoiding losing track of the current pupil. In order to do so, the dynamic illumination process can step up and down the camera's linear gain range until the second pupil is found, as depicted in FIG. 8. Points (a) and (b) in FIG. 8 delineate cases where the pupil is found to be at the edge of the desired pupil intensity range, and therefore a switch to searching in the other direction is performed, to avoid losing the pupil. At point (c), the second pupil is found and therefore the state is changed.

With a pre-set gain step size determined, the dynamic illumination process may begin at the camera mid-gain value and proceed to step up the gain range until it reaches the upper limit, then returning to the mid-gain value, and stepping down the gain range until it reaches the lower limit. The dynamic illumination controller 70 proceeds to do so until the second pupil is found, at which point the process transitions to a "Idealizing Pupils" state 96 as shown in FIG. 7A.

It may be noted that if the dynamic illumination controller 70 loses the first pupil at any point, the process may return to the searching for pupils state 94. It may also be noted that if the scene is quite variable, a saw-tooth function can be implemented (as opposed to returning immediately to the midpoint of the range after reaching the top or bottom of the range). Moreover, the dynamic illumination process can be configured to increase or decrease the shutter duration once it has reached the limits of the gain range, to ensure it has cycled through the full range of the found pupil's accepted illumination.

In order to determine that the first pupil is not lost from the search, an upwards or downwards motion stepping can be halted if the pupil's brightness is outside of set limits. For example, the limits used may include a sub range of the "Center Pupil Brightness" criteria used by the pupil candidate filtering process described below. As such, by stepping up or down, the dynamic illumination process can ensure that it would not cause the filtering process to consider an actual pupil as a false positive and reject it. By doing so, it can be ascertained that the system 10 still functions accurately with only one pupil in the scene, and thus is more robust.

Idealizing Pupils

In the idealizing pupils state 86, both pupils have been found and the objective in this state is to maintain or move the pupil intensity values as close as possible to the ideal pupil brightness to maintain the system in the ideal state, while ensuring both pupils maintain "in view" and are tracked consistently.

The process used herein can compare each pupil's brightness and determine which is furthest from the ideal pupil brightness. The dynamic illumination controller 70 may then determine the direction needed to move the camera gain and/or shutter in order to make the pupil closer to the ideal. In order to inhibit losing the other pupil, the dynamic illumination controller can be configured to check that the other pupil is within a determined acceptable pupil range, for example, the same range described in the finding other pupil state 92, described above. If so, the dynamic illumination controller 70 increments or decrements the camera gain by the gain step size. Otherwise, it maintains the current camera intensity parameters.

The idealizing pupil state 96 is illustrated in FIGS. 9 and 10. In FIG. 9, Pupil 2 is further from the ideal pupil brightness than Pupil 1, therefore the direction the whole setup needs to move in order to get it closer to the ideal brightness is determined. Since Pupil 1 is still within the acceptable pupil brightness range, the motion is allowed. Similarly, in FIG. 10, Pupil 1's brightness is furthest from the ideal, therefore the direction is determined based on that brightness. However, since Pupil 2 is outside the acceptable pupil brightness range, a camera intensity change does not need to be performed.

As described above, the single-user state diagram described in FIG. 7A can be modified to account for multiple users in the scene. FIG. 7B describes a similar state diagram, where the "Searching for Pupil" state is replaced with a "Continuously Scanning for Pupils" state. Similar to the initial state in the single-user case, found pupils are stored, with their intensity and positions in the scene contained in a similar storage container. Distinguishable from the original state, however, this state does not need to switch to the "Finding other Pupil" state until it has received an external signal for the location of the desired user to be tracked. The external signal may include a screen coordinate corresponding to the location of the desired user, as obtained from an external user location system. Once the signal is received, the closest pupil to the screen point is determined and, if within an accepted distance threshold, the system switches to the "Finding other Pupil" state. Additionally, at any point the system may receive an external signal to switch tracked users. In such a case, the system returns to the initial state.

Note that the described multi-user state diagram still only tracks a single user at a time, but permits selection of which user to track via an external signal. The reason for this has been found to be that: unless the reflectivity properties of the users are similar, a dynamic illumination system 10 having one modifiable illumination source may only be able to track one user at a time. However, if the gaze tracking apparatus permits separate effective illumination switching of multiple sub-sections of the scene (via a complex set of illumination sources, or region-of-interest camera parameter switching, for example), this can easily be expanded to track multiple users. In such a situation, the system would include n sub-sections of the scene, each with their own 1 to m illumination variation parameters. Thus, the described single-user state diagram could be implemented in each sub-section, allowing single user tracking within each sub-section of the scene. Alternatively, the state diagram described in FIG. 7B can also be implemented for each sub-section. Such a system would include n external control signals, and would permit multiple users per sub-section of the scene.

Figure 11:
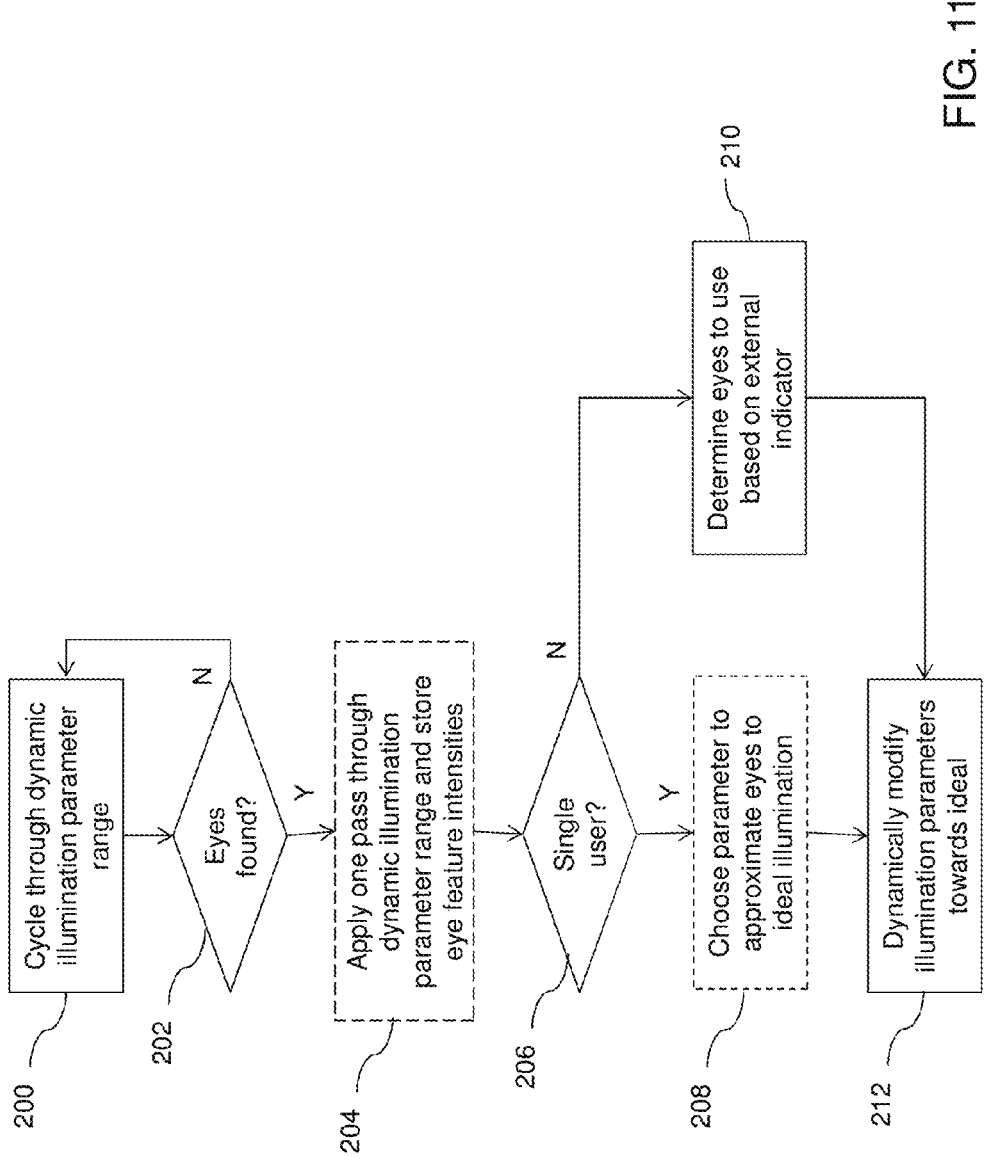
FIG. 11 is a flow chart illustrating example computer executable operations that may be performed in a dynamic illumination procedure.

Referring to FIG. 11, the dynamic illumination process performed by the dynamic illumination controller 70 can be described as follows. At 200, the dynamic illumination controller 70 cycles through the dynamic illumination parameter range while eyes have not been found and determines at 202 whether or not an eye has been found. If an eye has been found, the dynamic illumination controller 70 can optionally finalize one pass through the dynamic illumination parameter range at 204 (as illustrated in dashed lines in FIG. 11), storing eye feature intensities for each available eye. The dynamic illumination controller 70 then determines at 206 whether there is a single user or multiple users in the scene. If a single user exists in the scene, the dynamic illumination controller 70 chooses the dynamic illumination parameter that best approximates the available users eyes to the ideal illumination at 208 or, if step 204 was skipped, proceeds straight to step 212. If multiple users are expected in the scene, the dynamic illumination controller 70 determines the eyes to use based on the distance metric of the found eyes from an external indicator for the user of interest at 210.

Once a user's eyes are being tracked, the dynamic illumination controller 70 dynamically modifies the illumination parameters at 212 such that the user's eyes remain as close as possible to the ideal illumination. The metric used to maintain the eyes near the ideal illumination are the eye feature intensities in this example.

It may be noted that the example flow graph described herein does not contain a step associated with finding or re-finding one or multiple lost eyes as provided in at least some examples. Although this will result in a more robust tracking experience when both eyes are expected to be tracked, it has been found to not be required by the system. For example, a gaze tracking system focused on tracking single eyes and not eye pairs may not have an interest in perfecting the eye pair.

On-Axis Eye Detection Technique

A common technique used by infrared-based eye gaze trackers for detecting a user's eyes involves thresholding the pupil 50 from the rest of the scene by first differencing the on-axis (bright) and off-axis (dark) images. Since the pupil 50 is bright due to the retro-reflective properties of the cornea in the on-axis image, and dark in the other, the resulting difference image should ideally just contain the pupils. This image would then be thresholded at a reliable level, resulting in the binary image containing the pupils. However, it has been found that in practice, additional issues such as noise caused by the differencing during user motion, and objects which show the same properties as the pupil, tend to add what can be a significant amount of false positives to the scene which needs to be filtered. Other systems, which use solely off-axis illumination, tend to perform fairly computationally expensive appearance-based methods of extracting and determining the eyes from the scene, such as template matching or multiple Haar-cascades classifiers.

To address these issues, the eye candidate detection 74 shown in FIG. 6 can be configured to advantage of the theorem that under on-axis ideal illumination conditions, the reflective properties of the user's iris 52 are noticeably lower than those of the rest of its face and its pupil 50 in the on-axis case, which studies have shown to be a reliable test set. It has also been found that studies on the reflective properties of human skin, the human iris, and the human pupil retina support these assumptions.

The above theorem implies that under ideal illumination, the user's pupils 50 can be easily extracted from the image. That is, using the knowledge that the contrast between the pupil and the iris 52 of a user's eyes will be one of the highest in the scene, binarizing the image to extract these objects can be made to be straightforward. The blobs in such an image then only need to be analyzed and filtered (e.g., via the on-axis eye candidate filtering technique described below), leaving only the actual pupils 50. The determined threshold used should be such that under ideal illumination, any user can be thresholded accordingly. It may be noted that in this example, the technique is dependent on the above-mentioned facets, namely that: a) the input image is under on-axis ideal illumination conditions, and b) the binary blobs can be correctly filtered, resulting in the actual pupils being selected. This can be particularly important, since the binary image may contain a large amount of noise, among them aspects of the user's face and potentially other noise in the scene.

Binarizing the image to extract binary blobs involves threhsolding the original image or a modified representation of the original image. The advantage of implementing such a procedure using the described system is that the object of interest, the eye, is more easily differentiable from other objects in the scene due to the strong contrast between the pupil 50 and iris 52. Although many different approaches can be taken given this prior knowledge, two examples for creating a binary image are described below. It may be noted that these examples are provided only to demonstrate the advantageous effect of the provided prior knowledge for illustrative purposes, and should not be considered exhaustive within the principles described herein.

Figure 12:
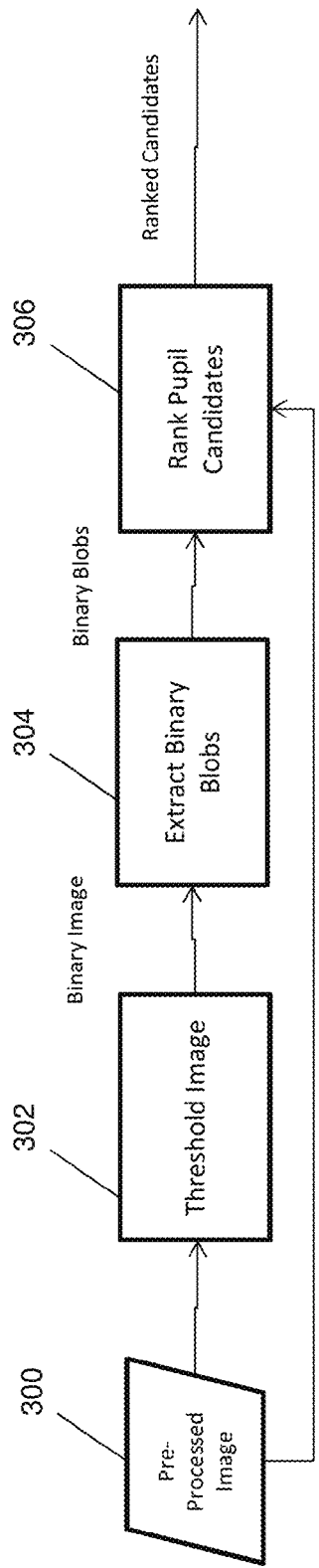
FIG. 12 is a flow chart illustrating an example of a process for on-axis eye candidate detection.

FIG. 12 illustrates one example of the eye candidate detection 74. At 300 a pre-processed image is obtained and the image is thresholded at 302 to generate a binary image. The binary image is then processed to extract binary blobs at 304 and these binary blobs are ranked as pupil candidates at 306. The approach shown in FIG. 12 can be applied when the image scene corresponds primarily to the user's face, and illumination constraints are not a particular concern. In such a case, the system 10 may attempt to threshold the image at an intensity value approximating that of the iris 52. By doing so, the skin 60 and pupil 50 should be segmented from the iris 52, and it follows that the skin 60 and pupil 50 will be separate. Whether or not such segmentation includes the sclera 54 may be inconsequential. It has been found that thresholding at the bottom ¼th of the illumination range of the camera sensor can be a reliable method of extracting the pupil 50 under such considerations.

Figure 13:
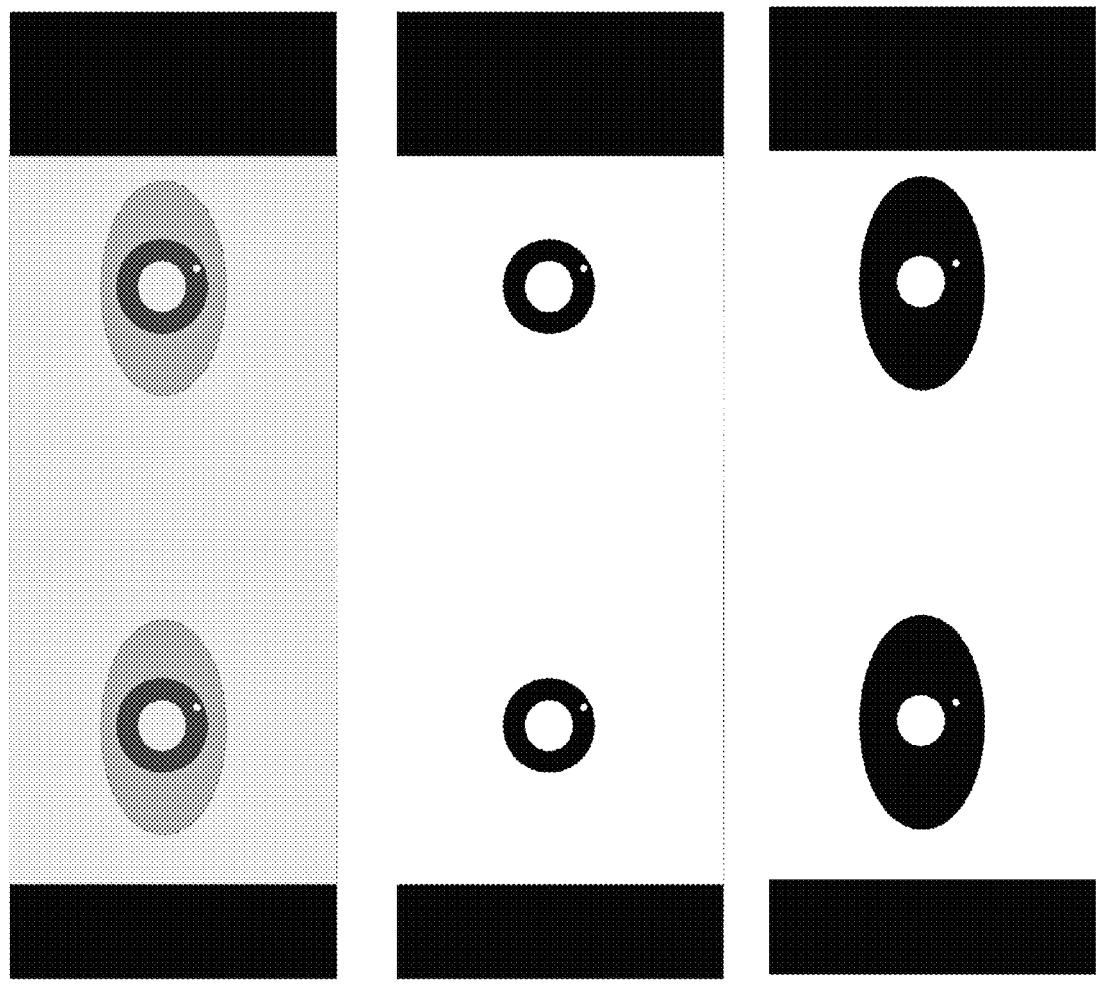
FIG. 13 illustrates the effect of on-axis thresholding applied within an on-axis eye candidate detection process using idealized illumination parameters.

FIG. 13 illustrates an example of the application of the process shown in FIG. 12 with on-axis thresholding within eye candidate detection under ideal illumination, where both exemplary binary images are potential results of the thresholding, whether the sclera 56 is linked with the face or not. The end result in this example would be obtaining binary blobs corresponding to the actual pupils 50 and the whole or portions of the face, which would be filtered out at a later state.

Figure 14:
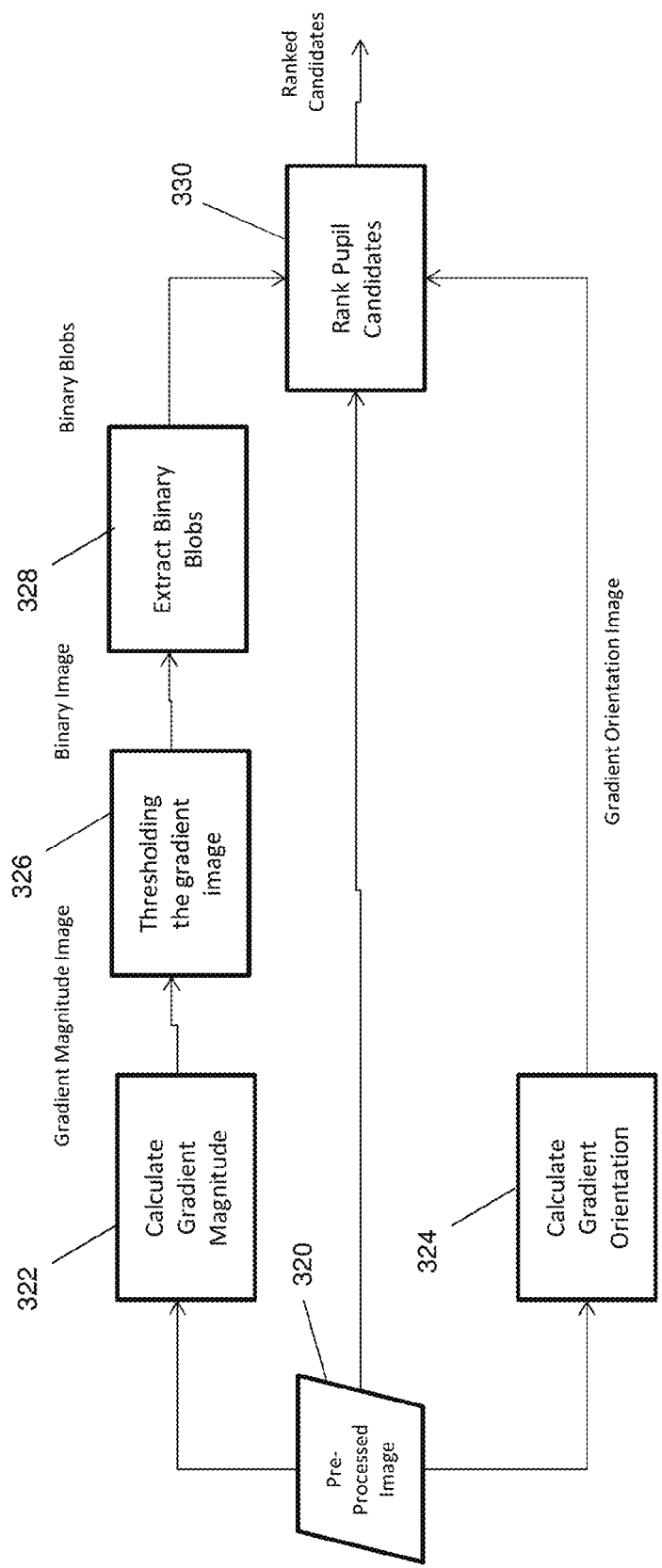
FIG. 14 illustrates a flow chart illustrating another example of a process for on-axis eye candidate detection.
Figure 15:
FIG. 15 illustrates an example of an on-axis image.
Figure 16:
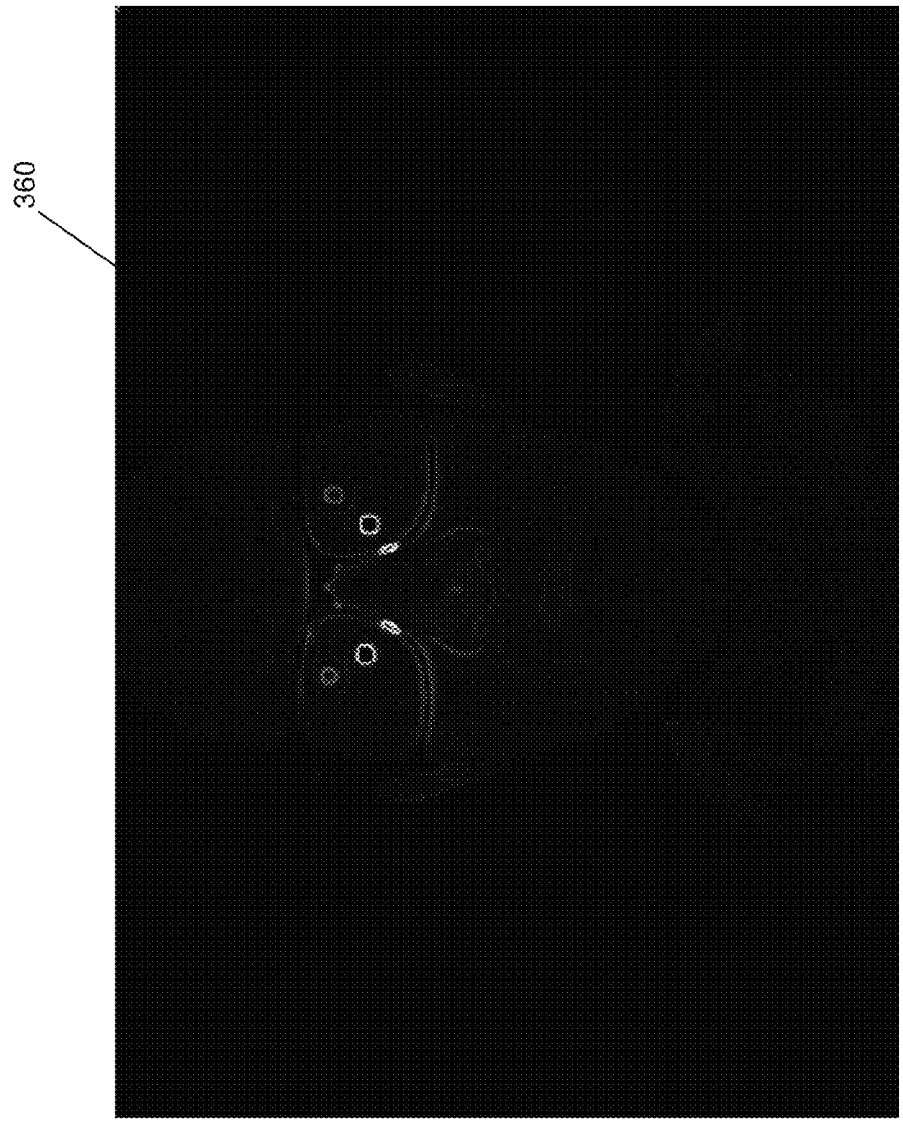
FIG. 16 illustrates an application of image gradient magnitude to the on-axis images of FIG. 15.
Figure 17:
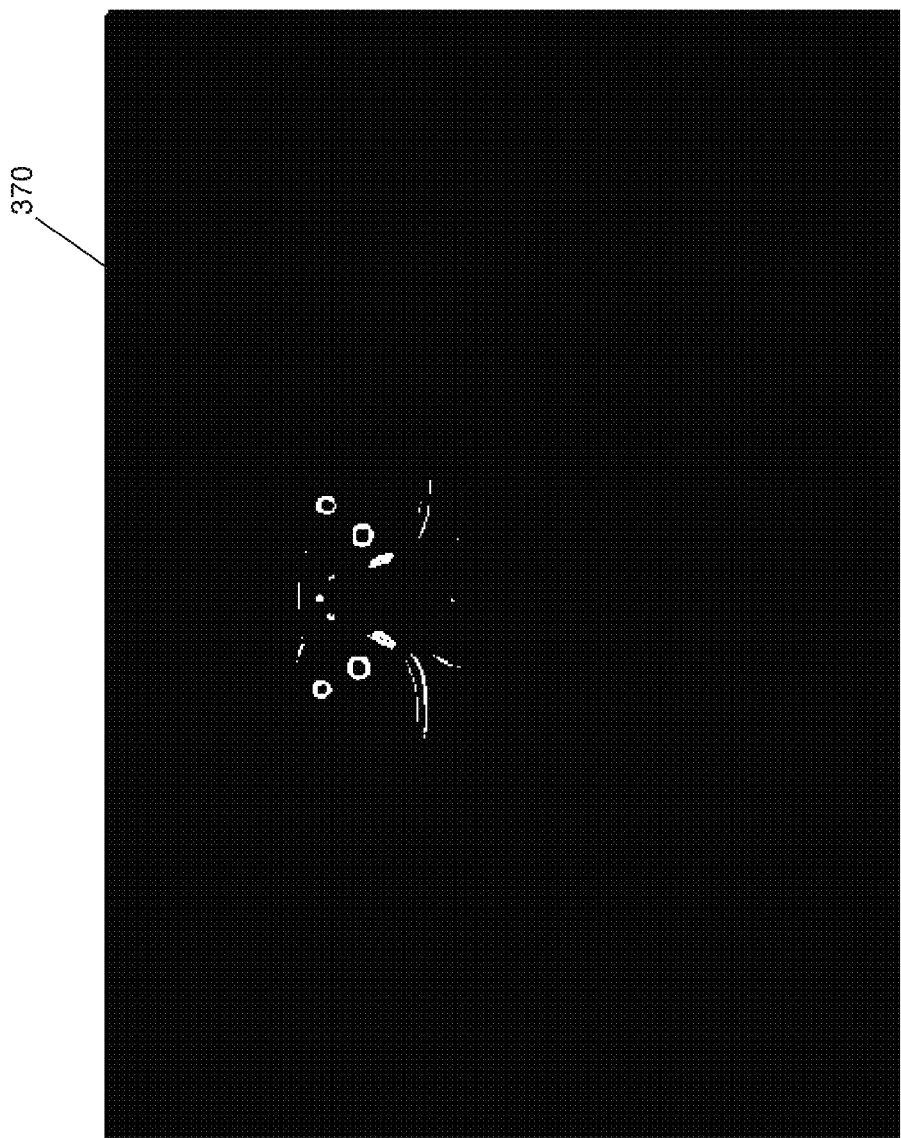
FIG. 17 illustrates an application of thresholding to the on-axis image of FIG. 15.

Turning now to FIG. 14, another example of a process for eye candidate detection 74 is shown. A pre-processed image (e.g., image 350 shown in FIG. 15) is obtained at 320 and this image is used to calculate a gradient magnitude at 322 and a gradient orientation at 324. Calculating the gradient magnitude generates a gradient magnitude image as illustrated in FIG. 16—image 360, which undergoes gradient thresholding at 326 to obtain a binary image, e.g., as shown in FIG. 17—image 370. The binary image is then processed at 328 to extract binary blobs, which are used with the gradient orientation to rank pupil candidates at 330.

The process shown in FIG. 14 includes analyzing the image gradient of the input image, and determining an appropriate threshold for it. This process takes into account imperfect illumination considerations, where additional illumination sources in the scene may make the simple thresholding above difficult to apply. Under such considerations, one may not be able to guarantee that the user's pupils will be able to reach the described ideal illumination in the scene. Also, the user's iris may not be within the expected intensity range from localized illumination making it brighter than expected. However, it can be assumed from prior knowledge of the scene that given the high retro-reflectivity properties of the human retina, the pupil should be one of the brightest objects in the scene. Additionally, one can presume that the iris 52 has a local minimal intensity. Thus, the gradient magnitude can be expected to be at the pupil-iris boundary one of the highest magnitudes in the scene.

It may be noted that the above assumptions do not apply when the system's illumination source is negligible relative to other illumination sources in the scene. As an example, if an on-axis apparatus 22 is used in broad daylight, and the effective sunlight illumination hitting the apparatus 22 is significantly higher than that of the apparatus's illumination source 32, the assumptions likely will not apply.

In order to reliably binarize the gradient magnitude image at 326, the system 10 can analyze the gradient magnitude histogram, searching for a threshold value which would binarize a top percentage P_threshold of the image, where:

$$P\_threshold=percentage(eyes)+percentage(expected\ high\ contrast\ objects)$$

Thus, a binarized image can be created which contains gradient magnitude binary blobs corresponding to the top P_threshold percentage of edges in the scene. Both the proportion of the gradient signal corresponding to the eyes and that corresponding to other expected high contrast objects should use the maximum possible size and quantity of both of these, for the application described.

As an example, for an application where only one user's eyes are being tracked at a given depth range, and the scene includes only the user's face, the system 10 can calculate the maximum expected size of the pupils (given the statistical variation in human pupil size and the operating range where the user is expected to be situated). For ideal binarization, a set proportion can be added, corresponding to the other expected high contrast objects (such as glasses glare), and threshold accordingly.

On-Axis Eye Candidate Filtering Algorithm

Figure 18:
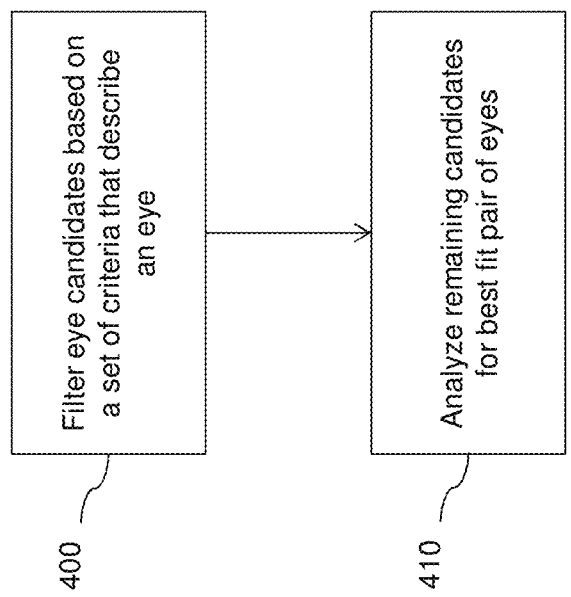
FIG. 18 is a flow chart illustrating example computer executable operations that may be performed in an eye candidate filtering procedure.

In order to ensure that the eyes are tracked accurately, the system 10 is configured to select eyes in the binary image amongst what can be considerable amounts of noise. Turning now to FIG. 18, a two-step process may be employed to filter eyes from the binary image. At 400, all eye candidates are filtered based on a set of criteria determined to best describe an eye and at 410, the remaining eye candidates are analyzed for the "best fit" pair of eyes.

Eye Candidate Filtering

The method used to filter most eye candidates can be based on a machine learning methodology for creating reliable features, for example, considering that a large number of simple feature metrics tend to compound to provide a reliable and robust feature. Each feature described is set with a given range within which an actual pupil is considered to acceptably lie under idealized on-axis illumination conditions. Each eye candidate is then analyzed for all the features. If the eye candidate fails to lie within the range of one of them, it is removed from the candidate list. Alternatively, a weighted feature set can be implemented, where suitable pupil candidates are those with a weighted sum of features above a certain threshold.

In the system described, the following features may be used to filter pupil candidates:

Pupil Roundness/Circularity:

regardless of the pupil's position in the eye, its roundness is fixed within a certain range that other objects typically fall outside of.

Pupil Intensity Distribution:

under ideal illumination, one can reliably expect the pupil's brightness values to fall within a certain fixed range. By doing so, it can easily be differentiated from common false positives such as glasses glare, which tend to have very high brightness values. In this example, the system 10 is configured to consider average pupil intensity, center pupil intensity (a central cross-section of the pupil), and pupil intensity variance.

Pupil Area:

This metric allows small objects like simple noise, and large objects like the user's face to be easily filtered out.

Iris Intensity Distribution:

As the portion of the outer eye with the lowest reflective properties, we expect this feature to be within a lower bound region.

Gradient Magnitude:

Related to the pupil and iris brightness metrics, it is expected that the gradient magnitude of the pupil-iris boundary to be within a certain range.

Gradient Orientation:

Although circularity and roundness are valuable metrics, the system 10 can additionally ensure reliable pupil candidates by accepting candidates with an inward-directed gradient orientation. That is, candidates with a signal intensity that increases as the signal moves from the iris to the pupil are accepted.

Fitted Ellipse Parameters:

considering that the found binary blob corresponds only to a rough estimate of the object, the provided data can be analyzed and fit to ellipses corresponding to the pupil and/or iris ellipses. This fits with our expectation of the pupil and iris being circular objects rotated to some extent off of the image plane axis. Thus, the pupil and iris objects imaged on the sensor will correspond to some form of ellipse. Consequently, roundness, circularity, and intensity distributions can also be analyzed based on the ellipse estimate of the object.

It may be noted that this example analyzes only features pertaining to the pupil and iris of the user's eye for illustrative purposes. A number of other features can be analyzed, such as the user's sclera, existence of corneal glints, and other facial features that would link a pupil candidate to a face. Additionally, all of these features could be combined into a common appearance-based matching approach, such as template matching or Haar-feature tracking. The variability in pupil size relative to the iris, eye size due to its position in the scene, pupil reflectivity, and the use of glasses makes training and testing of such classifiers relatively difficult and computationally expensive. Thus, in situations such as the present example, it may be preferable to have an independent analysis of each feature within supplied ranges.

Best Fit Eye Pair Matching

Once the majority of blobs have been removed, the pupil candidates are considered for the best pair, to be deemed eyes. If only one pupil is present, the highest ranked one is chosen. Finding the best pupil pair in this example includes comparing the described pupil features for each pair, attempting to find the most similar pair of eye candidates. This can be further enhanced by histogram matching of pupil candidates. In such an example, a successful pupil pair requires correlated histograms, as well as similar ellipse estimate dimensions and pupil intensity distributions. Additionally, knowledge of the inter-pupillary distance range between the pupils, as well as the potential size variability between them can further filter false positives.

On-Axis Gaze Estimation Techniques

As discussed above, subsequent to performing a feature extraction 78 for found eyes, the system 10 uses particular eye features to perform a gaze estimation 80.

On-Axis Normalized PCCR Mapping

Typical Pupil Center Corneal Reflection (PCCR) mapping gaze estimation systems take one or more vectors $\vec{V}_i$, defined as the vector between the pupil center $p_c$ and a corneal glint $g_i$, and using the one or more vectors, along with corresponding screen coordinates $s_i$, create a gaze estimation mapping. This is performed via a calibration procedure which takes known pairs of features F and screen points $s_i$, and performs a numerical fitting process to determine the coefficients of a functional mapping between them. Thus, a mapping function f(F) is created, where F is the set of features and f is the mapping function returning a screen point $s_i$. Although accurate when the user is static in the scene, these gaze mappings have been found to deviate often significantly from the correct point-of-gaze when the user modifies his or her three-dimensional position.

Figure 19:
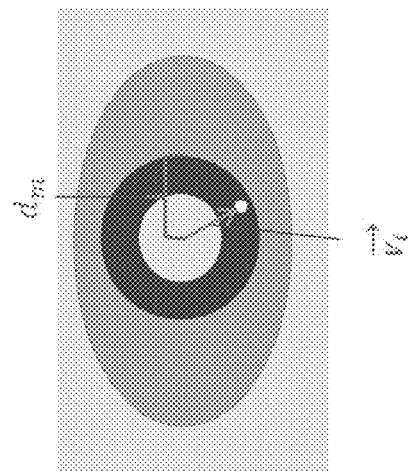
FIG. 19 illustrates an eye illuminated by the gaze tracking system with pupil-glint vector and a distance metric used to normalize the illustrated vectors.

To correct for this, one method, when two corneal glints 54 are available, is to normalize the supplied vectors $\vec{V}_i$ with a distance metric between the two corneal glints $d_g$ as shown in FIG. 19. Thus, $$\vec{V}_i \text{ becomes } \vec{V}_{Ni} = \frac{\vec{V}_i}{d_g}.$$

Figure 20:
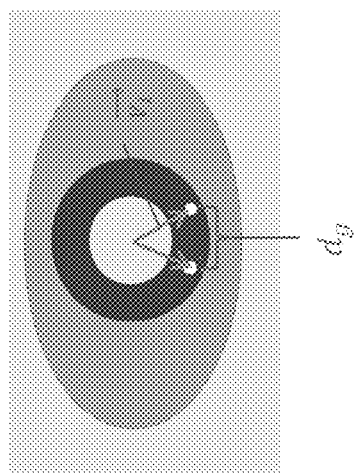
FIG. 20 illustrates an eye illuminated by the gaze tracking system with pupil-glint vector and a limbus distance metric used to normalize the illustrated vector.
Figure 21:
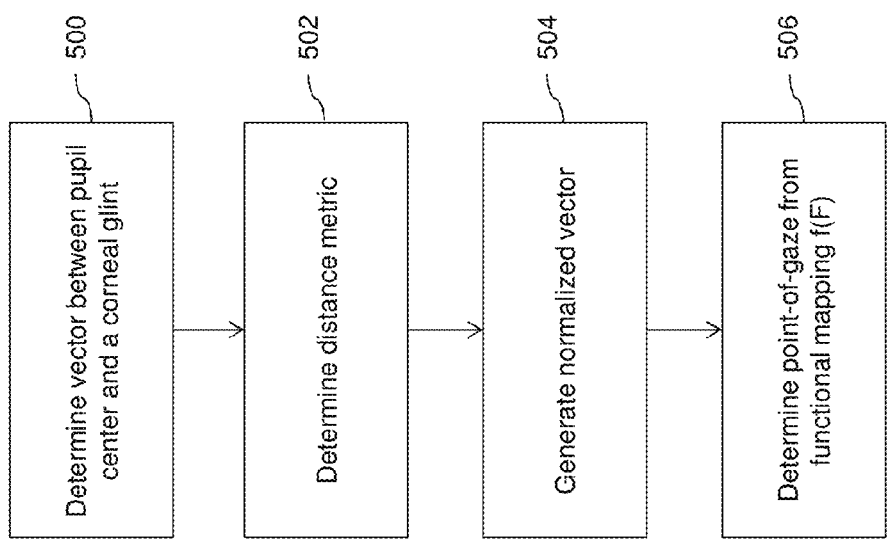
FIG. 21 is a flow chart illustrating example computer executable operations that may be performed in a gaze determination procedure.

This, then, corrects for user motion towards and away from the eye tracking apparatus 22, where the magnitude of the pupil-glint vector would vary when the user was looking at the same point $s_1$ on a screen. FIG. 19 depicts an eye illuminated under such a system, along with the vectors and distance metric described. In the example described herein and shown in FIG. 21, since the on-axis apparatus 22 only creates a single corneal glint on each eye, using this standard normalized vector is not performed. Instead, a $$\text{normalized vector } \vec{V}_{Ni} = \frac{\vec{V}_i}{d_m} \text{ is}$$

used as shown in FIG. 20, where $d_m$ is a distance metric that can correct for depth displacement. As shown in FIG. 21, the vector between the pupil center and corneal glint is determined at 500, the distance metric is determined at 502, and the normalized vector is generated at 504 using the values obtained at 500 and 502. This normalized vector is then passed into a functional mapping f(F) at 506, which outputs an estimated point-of-gaze on the screen.

Various distance metrics can be used to normalize the vector, including:

Limbus Distance Metric:

With this metric, the distance between the center of the pupil and the iris/sclera boundary (limbus) would be used. Various approaches for extracting the limbus may be used, e.g., those used for performing biometric analysis via iris recognition. This can be further simplified by extracting one point on the $p_{limbus}$, given the pupil ellipse and corneal glint $g_i$. It can be assumed that the pupil ellipse and limbus ellipse are concentric circles on a common plane, at an offset angle from the image plane they are imaged at. Thus, the major axis of each of the ellipses formed on the image is a reasonable approximation of the each circle's radius. Consequently, the relationship between the two radii can be found by calculating the relationship between the two intersection points $i_{pupil}$ and $i_{limbus}$ (from the pupil ellipse and limbus ellipse, respectively) on any line intersecting with the pupil center, $p_c$. Therefore, given $p_{limbus}$ and the pupil ellipse, we extract the corresponding intersection point $i_{pupil}$ and determine the scalar relationship c by which the iris radius $r_{iris}$ is larger than the pupil radius $r_{pupil}$. Finally, the distance metric $d_m$, corresponding to the iris diameter, is calculated taking the pupil ellipse major axis $a_{pupil}$ (from the non-rotated ellipse equation $$\frac{x^2}{a^2} + \frac{y^2}{b^2} = 1)$$

and multiplying it by our scalar relationship c: $d_m = c * a_{pupil}$.

Inter-Pupillary Distance Metric:

Since there is ample knowledge of the human population variance in inter-pupillary distance, this has been found to be a suitable metric. This metric assumes a model that can correct for cases where the user's head pose is not parallel to the camera, due to yaw motion, and in this example involves measurement of the distance between the user's pupils to determine distance from camera. The correction for head pose could be solved by using a reliable other face feature that can be detected, such as a user's nose.

Image Focus-Based Distance Metric:

Here the distance metric is estimated based on the change in blur of particular objects in the scene. In this case, the pupil/iris boundary is chosen, but other boundaries in the image (e.g. other eye or facial feature boundaries) can be chosen. This metric can be obtained via either depth from focus or depth from defocus. In depth from focus, the focus parameters are constantly switched such that the chosen object and object boundary are deemed in focus, with a focus criterion used to determine when the object has approximated perfect focus. In depth from defocus, the object's blur is analysed directly at any point in time. In both cases, the returned criteria is used to estimate the depth of the object from the imaging system. This depth can easily be used as the distance metric for our normalized vector.

Depth from Parallel System:

It is also possible that a depth estimate is readily available from a parallel system being used in conjunction with the described system, such as a range imaging system. In such a situation, the complexity of estimating depth is nullified.

Figure 22:
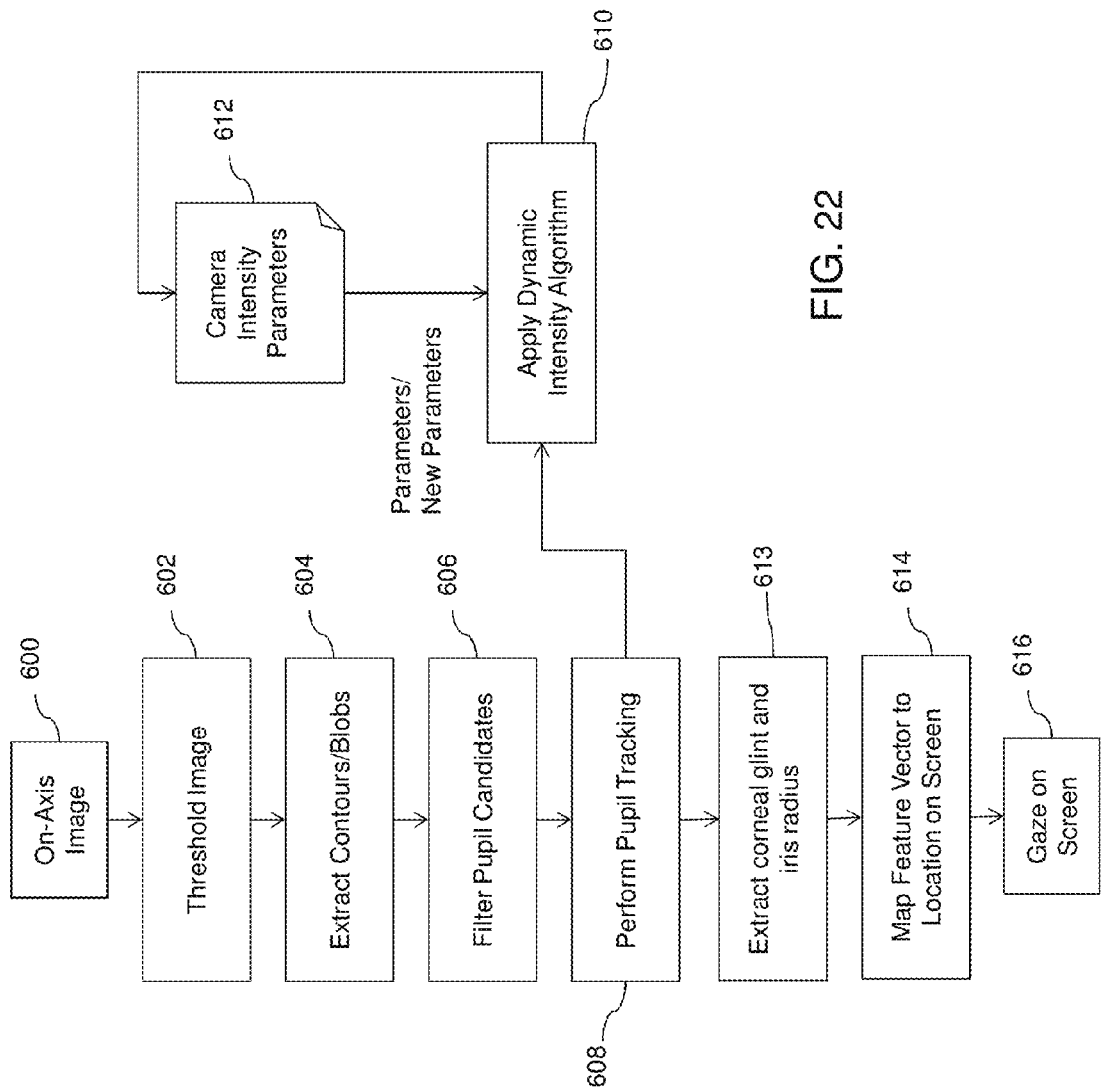
FIG. 22 is a flow chart illustrating example computer executable operations that may be performed by the gaze tracking system in an example implementation.

The system 10 may therefore be configured, in at least one example, to perform as shown in FIG. 22. At 600 an on-axis image is obtained, and a threshold image is generated at 602. The contours and blobs are then extracted at 604 from the thresholded image and the blobs are filtered for pupil candidates at 606. In parallel, the dynamic intensity process is applied at 610 and camera intensity parameters 612 updated and utilized on an ongoing basis to achieve the ideal illumination as discussed above. Pupil tracking is performed at 608 and in parallel, the dynamic intensity process is applied at 610 and camera intensity parameters 612 updated and utilized on an ongoing basis to achieve the ideal illumination as discussed above. The corneal glint and limbus radius are extracted at 613, and the described normalized feature vector is mapped to the location on the screen at 614 and the gaze on screen 616 is determined.

It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the system 10, any component of or related to the system 10, etc., or accessible or connectable thereto. Any application or module herein described may be implemented using computer readable/executable instructions that may be stored or otherwise held by such computer readable media.

The steps or operations in the flow charts and diagrams described herein are just for example. There may be many variations to these steps or operations without departing from the principles discussed above. For instance, the steps may be performed in a differing order, or steps may be added, deleted, or modified.

Although the above principles have been described with reference to certain specific examples, various modifications thereof will be apparent to those skilled in the art as outlined in the appended claims.

The invention claimed is:

1. A method of performing eye tracking, gaze tracking, or eye-gaze tracking, the method comprising, for a current image in a video feed from a single bright pupil effect imaging apparatus:
    dynamically updating one or more illumination control parameters of the imaging apparatus based on at least one illumination criterion, wherein the at least one illumination criterion was determined by analyzing at least one previous image in the video feed;
    acquiring a single image of a scene using the imaging apparatus under bright pupil effect illumination;
    processing the single captured image to detect at least one eye of a user and perform a gaze estimation;
    analyzing the scene, based on the current image and based on the at least one illumination criterion; and
    sending a request to update the one or more illumination control parameters towards a bright pupil effect optimized illumination based on the analyzing, wherein the updating of the one or more illumination control parameters is done for the acquiring of at least one subsequent image in the video feed.

2. The method of claim 1, further comprising outputting a point of gaze to an application.

3. The method of claim 1, wherein optimizing the illumination of the scene comprises modifying the illumination output by the illumination source, using the illumination detected by an imaging sensor.

4. The method of claim 1, wherein optimizing the illumination of the scene comprises at least one of: modifying an imaging sensor to modulate an amount of light received by the sensor, and modifying a signal received by the imaging sensor during acquisition of the single image.

5. The method of claim 1, wherein optimizing the illumination of the scene comprises:
    obtaining, at an illumination controller, illumination control parameters from the bright Pupil effect imaging apparatus and obtaining current eye feature parameters from the processing;
    generating, at the illumination controller, new illumination control parameters using the current eye feature intensity parameters; and
    providing, by the illumination controller, the new illumination parameters to the bright Pupil effect imaging apparatus during operation thereof.

6. The method of claim 5, wherein generating the new illumination parameters comprises:
    cycling through a range of values for one or more illumination parameters to find one or more eyes; and
    modifying the one or more illumination parameters towards an ideal when at least one eye can be found.

7. The method of claim 6, further comprising choosing a parameter to approximate eyes for the ideal.

8. The method of claim 7, further comprising determining eyes to use based on an external indicator when more than one user is detected in the scene.

9. The method of claim 6, further comprising applying a single pass through the range of values and storing eye feature intensities.

10. The method of claim 1, wherein the processing comprises performing an eye detection.

11. The method of claim 10, wherein the eye detection comprises performing an eye candidate detection and using a set of one or more eye candidates to perform an eye candidate filtering.

12. The method of claim 11, further comprising using a set of one or more found eyes to perform an eye feature extraction.

13. The method of claim 12, wherein a set of one or more eye features is used to perform the gaze estimation.

14. The method of claim 11, wherein the eye candidate filtering comprises:
    filtering eye candidates based on at least one criterion describing an eye; and
    analyzing remaining candidates for a best fit pair of eyes.

15. The method of claim 10, wherein the eye detection comprises at least one of the following steps:
    a. Performing image pre-processing on the captured image;
    b. extracting one or more binary blobs from a binary image;
    c. ranking pupil candidates using the binary blobs;
    d. providing a set of one or more ranked eye candidates;
    e. thresholding the captured image to obtain the binary image based on expected eye feature intensities;
    f. calculating a gradient orientation image and a gradient magnitude image from the captured image; or
    g. applying thresholding to the gradient magnitude image to obtain the binary image based on expected contrasts between eye feature intensities.

16. The method of claim 10, wherein the eye detection comprises:
    calculating a gradient orientation image and a gradient magnitude image from the captured image;
    computing the expected Proportion of the image which is to be covered by the user's eyes, under the assumption that the user is at the closest distance within a predefined operating range;
    determining the magnitude threshold on the gradient magnitude image such that the highest magnitude pixels within the defined Proportion are accented;
    thresholding to the gradient magnitude image to obtain the binary image based on expected contrasts between eye feature intensities;
    extracting one or more binary blobs from the binary image;

ranking Pupil candidates using the binary blobs; and
providing a set of one or more ranked eye candidates.

17. The method of claim 1, wherein the gaze estimation comprises:
    determining a vector between a pupil center and a corneal glint for a found eye;
    determining a distance metric;
    generating a normalized vector using the distance metric and the vector between the pupil center and the corneal glint; and
    determining a point of gaze from a functional mapping of the normalized vector.

18. The method of claim 17, wherein the distance metric uses any one or more of: a limbus diameter or radius, a pose-corrected interpupillary distance, other known eye or facial feature relationships, a depth of focus or de-focus metric, and at least one externally provided distance metric.

19. The method of claim 1, further comprising performing image pre-processing on the captured image.

20. The method of claim 1, wherein the bright Pupil effect imaging apparatus is coupled to an electronic device configured to utilizing eye tracking in at least one operation.

21. A method of performing eye detection for an eye gaze tracking system, the method comprising:
    receiving a single image of a video feed captured using a bright Pupil effect imaging apparatus under an optimized illumination created by dynamically updating one or more illumination control parameters prior to the capturing of the single image based on an analysis of at least one illumination criterion of at least one previous image in the video feed, to provide an expected degree of contrast between eye feature intensities for the current image; and
    performing an eye detection on the captured image.

22. The method of claim 21, wherein the eye detection comprises performing an eye candidate detection and using a set of one or more eye candidates to perform an eye candidate filtering.

23. The method of claim 22, further comprising using a set of one or more found eyes to perform an eye feature extraction.

24. The method of claim 23, wherein a set of one or more eye features is used to perform the gaze estimation.

25. The method of claim 21, wherein the eye detection comprises at least one of the following steps:
    a. performing image pre-processing on the captured image;
    b. extracting one or more binary blobs from a binary image;
    c. ranking pupil candidates using the binary blobs;
    d. providing a set of one or more ranked eye candidates;
    e. thresholding the captured image to obtain the binary image based on expected eye feature intensities;
    f. calculating a gradient orientation image and a gradient magnitude image from the captured image; and
    g. applying thresholding to the gradient magnitude image to obtain the binary image based on expected contrasts between eye feature intensities.

26. The method of claim 21, wherein the eye detection comprises:
    calculating a gradient orientation image and a gradient magnitude image from the captured image;
    computing the expected proportion of the image which is to be covered by the user's eyes, under the assumption that the user is at the closest distance within a pre-defined operating range;
    determining the magnitude threshold on the gradient magnitude image such that the highest magnitude pixels within the defined proportion are accepted;
    thresholding the gradient magnitude image with the determined magnitude threshold to obtain the binary image based on expected eye feature intensities;
    extracting one or more binary blobs from the binary image;
    ranking pupil candidates using the binary blobs; and
    providing a set of one or more ranked eye candidates.

27. The method of claim 21, wherein the eye candidate filtering comprises:
    filtering eye candidates based on at least one criterion describing an eye; and
    analyzing remaining candidates for a best fit pair of eyes.

28. A gaze tracking system comprising a processing module and computer executable instructions for operating the processing module performing eye tracking, gaze tracking, or eye-gaze tracking, for a current image in a video feed from a bright pupil effect imaging apparatus, comprising instructions for:
    dynamically updating one or more illumination control parameters of the imaging apparatus based on at least one illumination criterion, wherein the at least one illumination criterion was determined by analyzing at least one previous image in the video feed;
    acquiring a single image of a scene using the imaging apparatus under bright pupil effect illumination;
    processing the single captured image to detect at least one eye of a user and perform a gaze estimation;
    analyzing the scene, based on the current image and based on the at least one illumination criterion; and
    sending a request to update the one or more illumination control parameters towards a bright pupil effect optimized illumination based on the analyzing, wherein the updating of the one or more illumination control parameters is done for the acquiring of at least one subsequent image in the video feed.

29. The gaze tracking system of claim 28, further comprising the bright pupil effect imaging apparatus.

30. The gaze tracking system of claim 28, coupled to an electronic device.

31. The gaze tracking system of claim 30, wherein the gaze tracking system is integral to the electronic device.

32. The gaze tracking system of claim 28, wherein the bright pupil effect imaging apparatus comprises at least one illumination source and an imaging sensor.

33. The gaze tracking system of claim 32, wherein the imaging sensor is a camera.

34. The gaze tracking system of claim 32, wherein the at least one illumination source comprises an array of illumination sources surrounding the imaging sensor.

35. The gaze tracking system of claim 28, wherein the processing module comprises an illumination controller coupled to the bright pupil effect imaging apparatus.

36. A non-transitory computer readable medium, comprising computer executable instructions for performing eye tracking, gaze tracking, or eye-gaze tracking, for a current image in a video feed from a bright pupil effect imaging apparatus, comprising instructions for:
    dynamically updating one or more illumination control parameters of the imaging apparatus based on at least one illumination criterion, wherein the at least one illumination criterion was determined by analyzing at least one previous image in the video feed;
    acquiring a single image of a scene using the imaging apparatus under bright pupil effect illumination;

processing the single captured image to detect at least one eye of a user and perform a gaze estimation;
analyzing the scene, based on the current image and based on the at least one illumination criterion; and
sending a request to update the one or more illumination control parameters towards a bright pupil effect optimized illumination based on the analyzing, wherein the updating of the one or more illumination control parameters is done for the acquiring of at least one subsequent image in the video feed.

* * * * *

UNITED STATES PATENT AND TRADEMARK OFFICE
CERTIFICATE OF CORRECTION

PATENT NO. : 9,733,703 B2  
APPLICATION NO. : 14/626288  
DATED : August 15, 2017  
INVENTOR(S) : Nicholas J. Sullivan Page 1 of 1

It is certified that error appears in the above-identified patent and that said Letters Patent is hereby corrected as shown below:

In the Claims

In Line 65 of Column 17, Line 5 of Column 18, and Lines 1 and 21 of Column 19, delete "Pupil" and replace with "pupil".
In Claim 16, Column 18, Line 62 delete "Proportion" and replace with "proportion".
In Claim 16, Column 18, Line 62 delete "accented" and replace with "accepted".

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*